United States Patent [19]

Redding, Jr.; Bruce K.

[11] Patent Number: 5,460,756
[45] Date of Patent: * Oct. 24, 1995

[54] METHOD FOR ENTRAPMENT OF LIQUIDS IN TRANSFORMED WAXES

[76] Inventor: Bruce K. Redding, Jr., 2708 S. 86th St., Philadelphia, Pa. 19153

[*] Notice: The portion of the term of this patent subsequent to May 11, 2010 has been disclaimed.

[21] Appl. No.: 60,248

[22] Filed: May 11, 1993

Related U.S. Application Data

[63] Continuation-in-part of Ser. No. 505,849, Apr. 6, 1990, Pat. No. 5,209,879.
[51] Int. Cl.$^6$ ............................ B29C 39/10; B29B 13/08; B29K 91/00
[52] U.S. Cl. ...................... 264/4; 204/157.62; 264/442; 425/174.2; 425/803
[58] Field of Search ........................... 264/4, 4.1, 23, 264/69, 325, 330, 345; 106/270, 271; 425/803, 174.2; 204/157.15, 157.42, 157.62

[56] References Cited

U.S. PATENT DOCUMENTS

| | | | |
|---|---|---|---|
| 4,288,398 | 9/1981 | Lemelson | 264/23 |
| 4,324,756 | 4/1982 | Kepes et al. | 264/322 |
| 5,209,879 | 5/1993 | Redding, Jr. | 264/23 |

FOREIGN PATENT DOCUMENTS

| | | | |
|---|---|---|---|
| WO89/02814 | 4/1989 | WIPO | 264/4 |

*Primary Examiner*—Mathieu D. Vargot
*Attorney, Agent, or Firm*—Robert S. Lipton; Lipton & Stapler

[57] ABSTRACT

The method and apparatus of this invention entraps liquids within wax and transforms naturally occurring or synthetic waxes into a state characterized by the fact that when the waxes solidify, they do so in forms different from those forms into which they would solidify except for the transformation. The entrapment and transformation is achieved by subjecting the waxes to force. As examples of apparatuses which can supply the force to effect the transformation, a piston apparatus and an ultrasonic apparatus are disclosed. The triglyceride waxes are one type of wax which may be transformed by the method and apparatus of this invention. Transformed triglyceride waxes are superior hosts for liquids entrapped within their matrix. The subject method is particularly effective for minimizing loss of liquids due to volatilization the entrapment process.

10 Claims, 18 Drawing Sheets

METHOD FOR ENTRAPMENT OF LIQUIDS IN TRANSFORMED WAXES

This application is a continuation-in-part of patent application Ser. No. 07/505,849 filed Apr. 6, 1990, entitled Method For Inducing Transformations in Waxes, by Bruce K. Redding, Jr., now U.S. Pat. No. 5,209,879 issued May 11, 1993.

BACKGROUND OF THE INVENTION

The subject invention relates to a method and apparatus for the entrapment of liquids in fats, and more particularly to such method wherein liquid vaporization is minimized through pressure processing techniques which entrap volatiles within a stable lipid matrix. Accordingly, liberation of volatiles from the subject apparatus during processing as well as from the end-product is minimized.

Heretofore, retention of liquids in fats has been accomplished through a variety of techniques. Coacervation, interfacial polymerization, spray drying and granulation methods are illustrative of prior art teachings, but each is attendant with significant liquid losses during processing and afterwards, from their unstable end-products.

Many liquids, such as flavors and fragrance oils for example, contain a mixture of volatile alcohols and aromatics, which evaporate when exposed to even minimal heat. Indeed, many such substances often lose as much as 45% of their original weight during the encapsulation process due to volatilization. Such losses are wasteful and expensive. Additionally, resulting end-products of these methods often taste less poignant or smell less desirable than the original liquids.

The use of fats as a retention media for volatiles is disclosed in U.S. Pat. No. 3,949,094 of Johnson, et al. issued Apr. 6, 1976, wherein volatile flavorings, seasonings, colorants, flavor enhancers and the like are blended with lipoidal material under superatmospheric conditions for subsequent handling or conversion into particulates by a spray chilling process. While retention of the volatiles within fat under pressure reduces vaporization before processing, excessive losses are still experienced during the Johnson spray chilling encapsulation method. Furthermore, the Johnson and other similar spray-drying methods result in microcapsules of inferior quality as compared to the liquid/fat matrix product of the subject invention as described herein. In essence, the "sealing" effect of liquids within fats by prior art methods is often insufficient resulting in unwanted liquid oxidation, reduction or volatilization, particularly when the capsules are exposed to mechanical shear during subsequent granulation processes.

Applicant has discovered that liquids may be entrapped within a stable lipid matrix rather than the capsules of the prior art. Before the subject method and apparatus for accomplishing same may be fully appreciated, however, the physical properties of lipids, such as fats and waxes, must first be understood.

Naturally occurring and synthetic waxes are extensively used in a wide cross-section of industries including the food preparation, pharmaceutical, cosmetic, and personal hygiene industries. The term wax is used to denote a broad class of organic ester and waxy compounds which span a variety of chemical structures and display a broad range of melting temperatures. Often the same compound may be referred to as either a "wax," "fat" or an "oil" depending on the ambient temperature. By whatever name it is called, the choice of a wax for a particular application is often determined by whether it is a liquid or solid at the temperature of the product with which it is to be used. Frequently it is necessary to extensively purify and chemically modify a wax to make it useful for a given purpose. Despite such efforts at modification, many physical characteristics of the waxes inherent in their structure still prevent them from being used successfully or demand that extensive additional treatments be undertaken.

For instance, extensive commercial use has been made of the naturally occurring carboxylic acids ("fatty acids") and their derivatives, most commonly the glyceryl derivatives in which all three hydroxy groups of the glyceryl molecule are esterified with a carboxylic acid. The carboxylic acids may be saturated or unsaturated. The tri-substituted glyceryls (triglycerides) are major components of most animal and plant fats/oils/waxes. When all three hydroxy groups of a glyceryl molecule have been esterified with the same fatty acid, it is referred to as a monoacid triglyceride. Whether one refers to triglycerides as "waxes," "fats," or "oils" depends upon the chain lengths of the esterified acids and their degree of saturation or unsaturation as well as the ambient temperature at which the characterization is made. Generally, the greater the degree of saturation and the longer the chain length of the esterified acids, the higher will be the melting point of the triglyceride.

An interesting feature of the triglycerides is that they may simultaneously solidify in more than one crystalline form within the same mass. This ability to exist in more than one crystalline state is termed "polymorphism" and is frequently observed among the waxes. Complicating the use of triglycerides even further is the fact that triglycerides exhibit a special form of polymorphism, designated monotropic polymorphism, in which the lower melting point crystal forms are unstable and convert over time to more stable forms, with the conversion dependent upon time and the temperature of the material. Monotropic polymorphism conversion always takes place in the direction towards the more stable crystal forms. Such conversion between polymorphic forms involves a structural rearrangement of the molecules.

For example, when melted, cooled, and solidified rapidly, the monoacid triglyceride glyceryl tristerate first hardens in a glass-like amorphous form which it then converts over time to a crystalline form (the alpha "α" form) having a hexagonal crystal lattice structure with a melting point of about 54° C. The polymorphic α form is only relatively stable. If heat is applied to α form material, the glyceryl tristerate will convert over time through an unstable intermediate form (the beta-prime "β'" form) to a yet higher melting point form (the beta "β" form), having a triclinic crystal lattice structure with a melting point of about 72° C. Once the conversion to the higher melting point β form is complete, the β form is stable. While many of the triglycerides, such as glyceryl tristerate, are available in relatively pure β form powders, these β forms are obtained from crystallization of the material from solvents into the powders. The powders themselves are usually not usable with processes which involve melting and resolidification since, once the triglyceride is melted and allowed to recrystallize, both the lower α and higher β melting point polymorphs are present in the resulting material.

Such polymorphism presents problems in the formulation of products using triglyceride waxes as well as in the stability of the products over time. The commercial use of the polymorphic materials often requires extensive treatment of the product to convert the triglycerides to the β form. If this is not done, the coexisting α and β forms will slowly rearrange over time within the product to convert the material in the α form to material in the β form. This rearrangement is both time and temperature dependent and may produce many undesirable features in the product. Thus, in preparation of such common foods as chocolates (to which triglycerides are added to affect the sense of taste), it is often necessary during processing to repeatedly cycle the temperature of the chocolate over a period of time to convert the residual α form triglycerides to β form. If the temperature is not cycled, the chocolate may well show undesirable crystallization characteristics.

This "tempering" is a common feature of processes where polymorphic waxes and, in particular, triglycerides are used. Such tempering procedures must also take into account the characteristics of the compounds with which the waxes are mixed, presenting a complex problem of how to treat the entire mixture.

Similar problems arise when waxes are used as coating materials in encapsulation processes. Often the wax coating fails to shield the coated material as intended. An examination of the physical structure of such wax coats indicates that fissures and cracks develop in the coating. Certainly for the polymorphic waxes, the transition between polymorphic forms (with the associated structural rearrangement of the molecules into different crystal structures) is inconsistent with the coating/encapsulation requirement that the coating material posses a stable structure over time. Further, wax coatings containing both polymorphic forms tend to lack physical strength and be poor moisture barriers. Although polymorphic waxes may eventually convert substantially to the stable higher melting point form as they age in a warm environment, this process can take a long time, leaving sensitive materials inadequately protected by such wax coating or shell layer. A coating made of such waxes provides little immediate protection for sensitive materials such as volatile flavoring and fragrance oils.

Nowhere in the prior art is it known how to treat waxes so that they solidify in a more stable state or, in the case of polymorphic waxes, in the stable β polymorphic form. Accordingly, and moreover, the entrapment of volatiles within such a stable state lipid has neither, heretofore, been accomplished.

SUMMARY OF THE INVENTION

It has been discovered that the subject method and apparatus is capable of entrapping volatile liquids within a stable lipid matrix end-product with minimal liquid loss due to vaporization, where such lipids are polymorphic waxes, the liquid droplets are evenly entrapped within the triclinic crystal lattice of the wax upon its transformation into the β form. The subject products are also characterized by enhanced resistance to volatilization, reduction and oxidation of their liquid counterparts as well as to shear forces upon exposure to mechanical processes. Additionally, it has been discovered that these pressurization treatments may be employed to increase the content of the target liquid within the lipid host as compared with prior art methods, and that a more homogeneous dispersion of the liquid within the lipid matrix results.

The method and apparatus of this invention transforms waxes which are in the liquid phase to a state from which the waxes solidify in a form having improved physical characteristics. For non-polymorphic waxes, the transformation yields a form of the waxes which exhibits improved coating characteristics such as the ability to prevent access to the coated material by water or other environmental conditions. Similar improved coating characteristics are seen for the polymorphic waxes which, in addition, as a result of the transformation, solidify in the stable higher temperature polymorphic form. For the widely used polymorphic wax, glyceryl tristearate, the method and apparatus of this invention yield a molten form which solidifies in the stable β polymorph. The starting material for the method of this invention may be either a microcrystalline form of the wax, a liquid form, or a previously melted and resolidified form. The wax is melted, if necessary to obtain a liquid phase, combined with the desired liquid, and subjected in the liquid phase to force. For instance, the liquid wax and volatile may be placed in a chamber attached to a piston and subjected to the force of the stroke cycles of the piston. As an example of another means for applying force, the liquid wax may be exposed to ultrasound delivered by an ultrasonic transducer immersed in the liquid wax. In another embodiment of the subject method, the liquid wax and liquid are simultaneously agitated and cooled slowly in an enclosed agitator reactor to produce a powder product within which the liquid is entrapped. The liquid transformed wax resulting from subjecting the wax to force exhibits improved physical characteristics and is particularly useful in encapsulating or entrapping materials without the use of solvents.

It is, therefore, a primary object of the subject invention to provide a means for entrapping liquids within a stable lipid matrix through the use of pressure processing techniques.

It is another primary object of the subject invention to provide a means for entrapping liquids within waxes with minimal loss of the liquids due to vaporization.

It is an object of this invention to provide a method for the transformation of naturally occurring and synthetic waxes which alters the physical state of the waxes to improve their characteristics.

It is an object of this invention to provide a process whereby polymorphic waxes may be transformed in the liquid phase to produce a liquid form of the wax which solidifies in the stable higher melting point polymorphic form.

It is another object of this invention to provide a process for transforming liquid waxes so that such waxes may be used in entrapment process as superior host materials.

An additional object of this invention to provide a process for transforming liquid waxes so that such ,waxes may be used in encapsulation processes as superior shell materials.

A further object of this invention is to provide a piston apparatus suitable for transforming waxes to a more stable state.

Another object of this invention is to provide an ultrasonic apparatus suitable for transforming waxes to a more stable state.

Other useful objects of the invention will become apparent to those skilled in the art from the disclosure which follows.

DETAILED DESCRIPTION OF THE INVENTION

The term "wax" as used in this application is intended to have as broad a meaning as possible and contemplates organic ester and waxy compounds derived from animals, vegetables, and minerals including modifications of such compounds from all three sources in addition to those materials having similar properties which are synthesized. Examples of some of the naturally occurring and synthetic waxes which may be used either alone or in combination with the method and apparatus of this invention are shown below in Table 1.

TABLE 1

| | |
|---|---|
| GLYCERYL TRISTEARATE | GLYCERYL DISTEARATE |
| DYNASAN ™ 110, 114, 116, 118 | STEROTEX ™ HM, K |
| CANOLA WAX/OIL | COTTON FLAKES |
| SOYA FLAKES | CASTOR WAX |
| RAPESEED WAX | BEESWAX |
| CARNAUBA WAX | CANDELILLA WAX |
| MICROWAX (PETROLEUM BASED) | BOLER ™ WAX 1014 |
| SPECIAL FAT ™ 42, 44, 168 T #195A | BE SQUARE ™ WAX |
| BE SQUARE ™ WAX #195W | ENERGYBOOSTER ™ |
| ASTOR ™ WAX 180 | ASTOR ™ WAX 150 |
| POLYETHYLENE POLYMERS | MELTABLE |

For purposes of disclosure in this application of the method and apparatus of this invention, it is convenient to consider and demonstrate the method and apparatus by their application to a class of commonly used waxes, the triglycerides.

In nature, triglycerides are usually found in association in complex mixtures. Depending upon the source of the triglyceride, whether animal or plant, the triglyceride may be formed from shorter or longer carboxylic acids which may in turn be either saturated or unsaturated. Triglycerides formed from shorter chain, unsaturated carboxylic acids, as a rule, melt at a lower temperature than triglycerides formed from longer-chain, saturated acids. In most cases, triglycerides are formed of more than one type of carboxylic acid. Further, the physical characteristics of a triglyceride (such as whether it exists as a liquid or solid at room temperature) are determined not only by which carboxylic acids were incorporated by esterification but also in which of the glyceryl hydroxy positions a given carboxylic acid was incorporated. Thus, animal triglycerides differ from plant triglycerides not so much in the overall ratios of saturated to unsaturated acids or of acids of given lengths, but rather in which of the three hydroxy positions in the glyceryl molecule unsaturated acids are to be found. Also, typically, naturally occurring triglyceride waxes which are solid at room temperature do not display a single sharp melting point because of the wide range of triglycerides present in most natural products.

Figure 1:
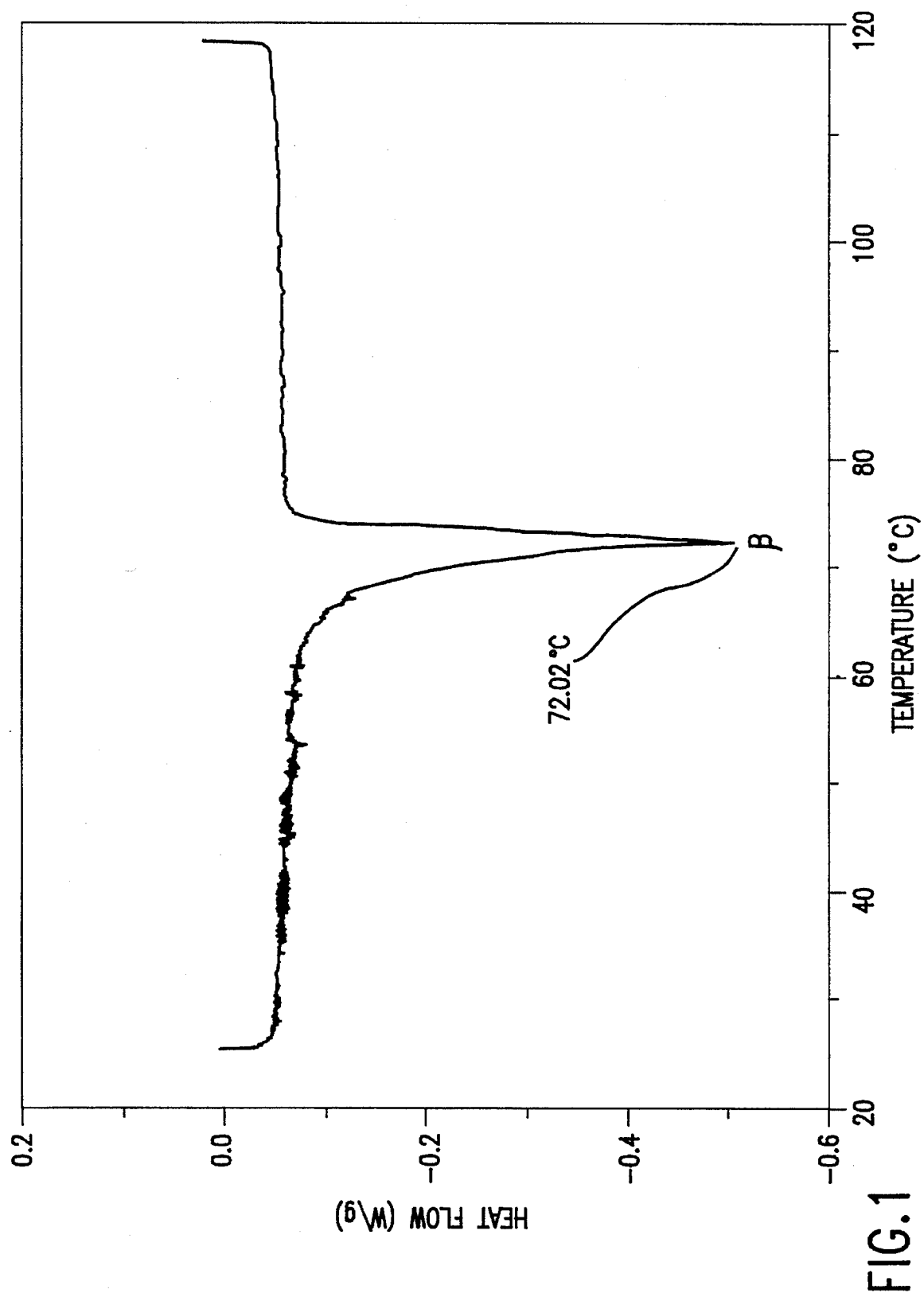
FIG. 1 is a differential scanning calorimeter (DSC) spectrum showing the endothermic melting point peak of the stable β polymorph of crystallized glyceryl tristerate (Dynasan 118) as provided by the manufacturer.

Triglyceride waxes may be obtained commercially with a choice of chain length of the carboxylic acids which form the triglycerides, as well as a choice of purity grades. Commercial preparations of triglycerides start with natural products in which a number of different triglycerides are associated with each other. Processing not only saturates the acid substituents but reduces the variety of triglycerides in the final material. The method and apparatus of this invention may be clearly demonstrated using the monoacid triglyceride, glyceryl tristerate ("tristearin") formed by the esterification of 18-carbon stearic acids with all three hydroxy groups of glyceryl. Stearic acid is a fully saturated carboxylic acid. The most suitable commercial grade of tristearin of which Applicant is aware is a product having the trademark "Dynasan 118" which is manufactured by Dynamit Nobel, a subsidiary of Huis America. Dynasan 118 is a highly purified material from a vegetable source which contains relatively few triglyceride molecules which have esterified acids of different lengths. Similar, although somewhat less pure triglyceride materials are also commercially available under the trademark Sterotex. As it is supplied by the manufacturer, Dynasan 118 is a white microcrystalline powder crystallized in the β form as can be seen by the differential scanning calorimeter (DSC) spectrum of a sample of Dynasan 118 shown in FIG. 1. The presence of only a single endothermic peak centered at approximately 72° C. indicates that only a single polymorphic form is present with a melting point within the melting point temperature range of the β form.

Figure 2:
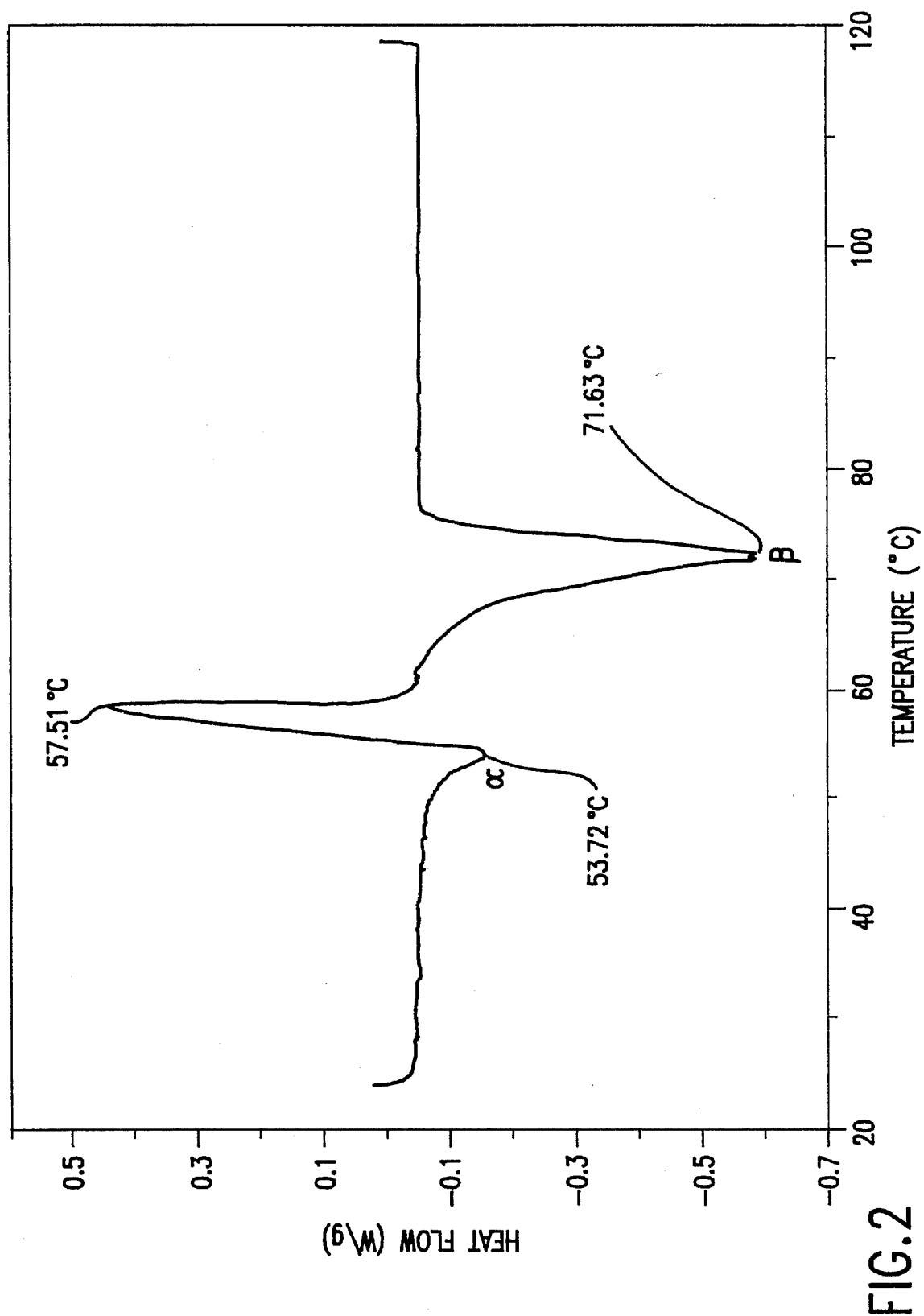
FIG. 2 is a DSC spectrum of glyceryl tristerate which has been melted and re-solidified showing the endothermic peaks corresponding to the α and β forms and the exothermic heat of crystallization.

Like other triglycerides, when the Dynasan 118 tristearin is heated to a molten phase and allowed to cool, it crystallizes in both the α and β polymorphic forms as can be seen in FIG. 2 where the Dynasan 118 was first heated to 125° C. and then resolidified. The polymorphic α form melts at a lower temperature and is seen in the DSC spectrum of FIG. 2 as an endothermic peak centered at approximately 54° C. The stable polymorphic β form melts at a higher temperature and is seen in the DSC spectrum of FIG. 2 as the more prominent endothermic peak centered at approximately 72° C. The resolidified tristearin obviously has coexisting within it both crystal structures. The upward (exothermic) peak) centered at approximately 57.5° C. between the endothermic peaks for the α and β forms in the DSC spectrum of FIG. 2 is the exothermic heat of crystallization. This Figure shows the classic DSC spectrum of the heat of crystallization of tristearin.

A few comments are in order with respect to the DSC spectra presented in the figures. First, the absolute height (or depth) of the peaks in the DSC spectra are reflective only of the mass of the sample used to generate that spectrum. Thus, differences in the height (or depth) of a peak from one spectrum to another are not significant in terms of identifying the polymorphic forms in which the material exists. The different polymorphic forms are distinguished by the fact that they melt at different temperatures.

The relative proportions of the polymorphic α and β forms which crystallize from melted tristearin will vary depending upon the heating and cooling regimen to which the tristearin sample has been subjected. However, FIG. 2 is representative of tristearin when it is melted and resolidified. It is obvious from the width of the peaks in the DSC spectra of FIGS. 1 and 2 that a range of melting points exist for both the α and β forms. The exact reason for this is unclear.

Applicant is aware of two possible explanations for the width of the peaks. First, it is suggested that even in the solid (crystallized) state, some non-ordered or randomly ordered tristearin may be trapped within the crystalline structures, thereby locally altering the crystal structure and its melting point. The second explanation is that, because of the nature of the commercial preparation of the tristearin, a totally pure, homogeneous material has not been obtained. For instance, not all of the stearic acid moieties may have been totally saturated. It is also possible that some shorter or longer chain carboxylic acids may have participated in the esterification, whether saturated or not. The range of compounds therefore yields a range of melting points which is reflected not only in the width of the DSC peaks but also in the fact that different samples have slightly different/shifted principal melting points. Applicant believes this second explanation is most likely. Applicant has observed that tristearins from different manufacturers and/or derived from different starting materials exhibit varying peak widths as well as slightly shifted melting points of the polymorphic forms as measured by the DSC. However, there may also be other factors at work which are unknown to the Applicant.

The discovery which is the subject of this invention is that the application of force to liquid phase waxes transforms the waxes into a different liquid state characterized by the fact that, when the waxes solidify, they do so in forms different from those forms into which they would solidify except for the application of force. The transformed waxes exhibit altered characteristics which make them more usable for manufacturing processes including liquid entrapment. This discovery is clearly demonstrated with respect to glyceryl tristearate. Discussion of the effects of the subject pressure processing techniques on this substance appears below followed by an examination of the same techniques employed to entrap liquids within transformed waxes.

Figure 3:
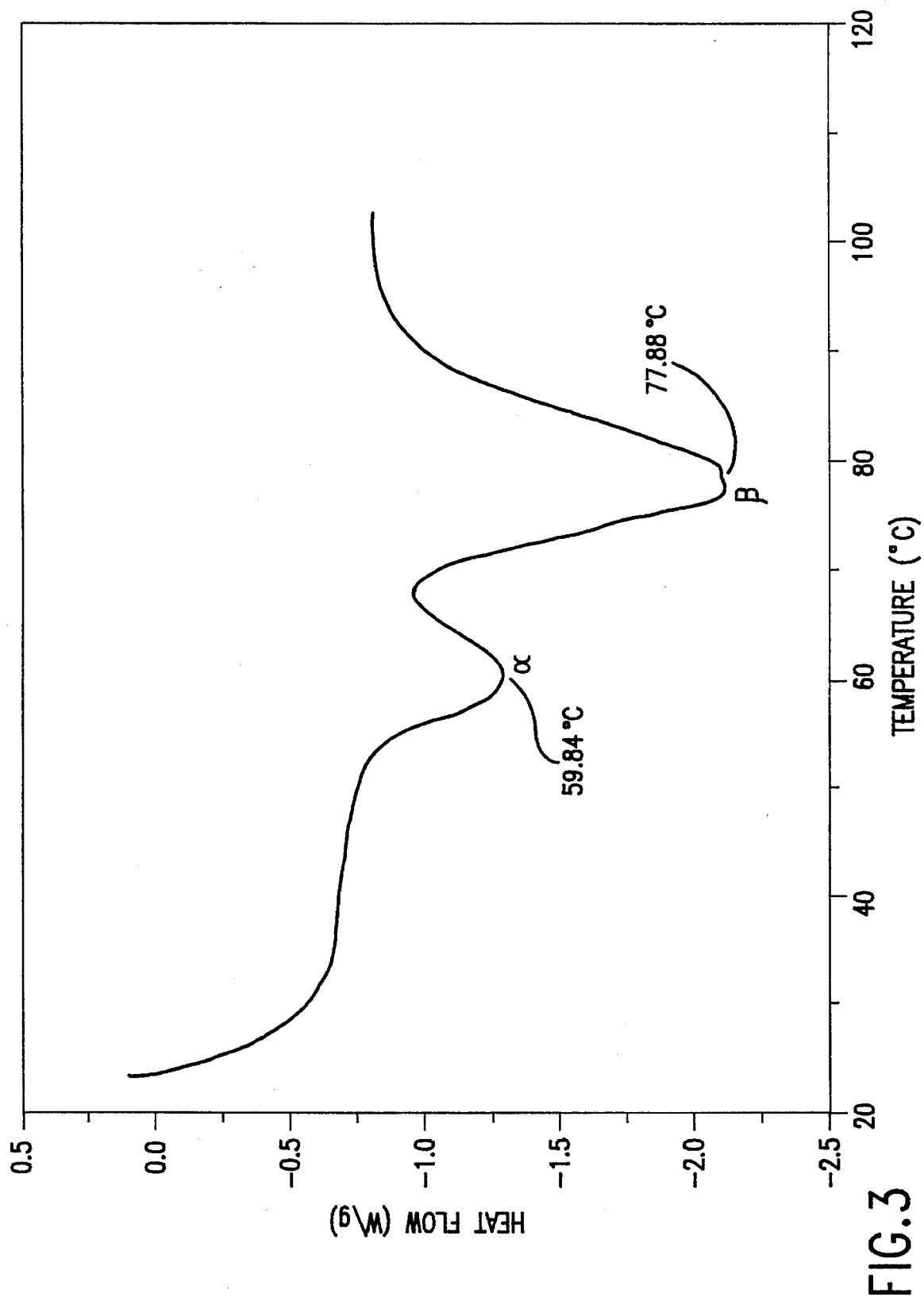
FIG. 3 is a DSC spectrum of glyceryl tristerate which has been melted to 90° C., subjected to the force of one piston stroke cycle, and resolidified.

FIG. 3 is the DSC spectrum of solidified tristearin which, while in the molten phase at 90° C., was subjected to the force of a single compression/expansion cycle of a piston stroke before solidification. Peaks corresponding to the polymorphic α and β forms of the tristearin are still evident and are identified by appropriate legends in the Figure. The lower melting point polymorphic α form shows a peak centered at approximately 60° C. while the higher melting point polymorphic β form shows a peak centered at approximately 78° C. The piston applied a maximum pressure to the wax of approximately 4400 pounds/inch$^2$ during the stroke cycle.

Figure 4:
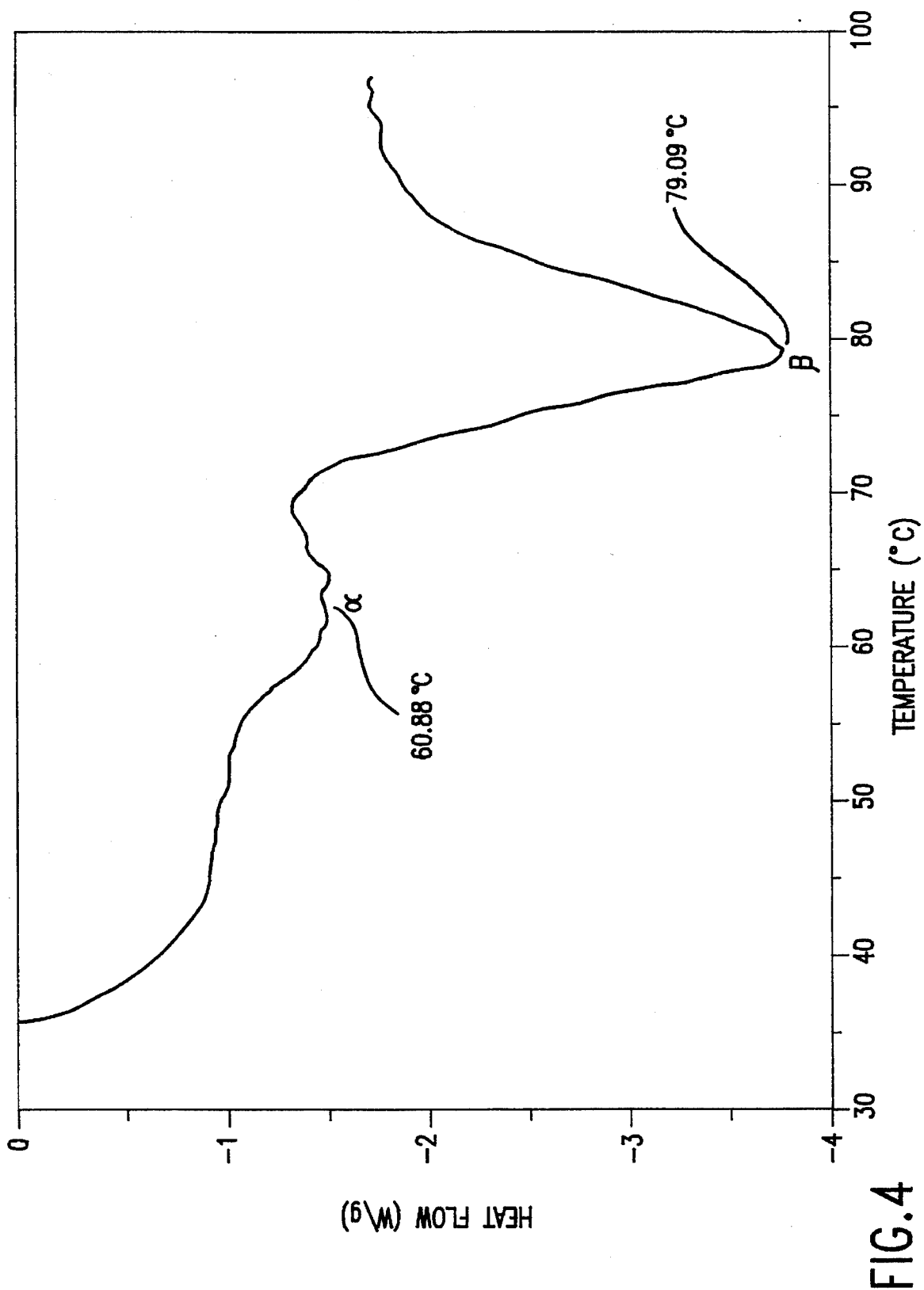
FIG. 4 is a DSC spectrum of glyceryl tristerate which has been melted to 90° C., subjected to the force of five piston stroke cycles, and resolidified.

FIG. 4 is a DSC spectrum of solidified tristearin which, while in the molten phase at 90° C., was subjected to the force of five compression/expansion cycles of a piston stroke before solidification. It can clearly be seen that a significantly smaller percentage of the material solidified in the polymorphic a form than in the polymorphic β form when compared to the material subjected to the force of a single stroke cycle of FIG. 3. The additional force applied by the piston stroke cycles to the material of FIG. 4 clearly transformed the molten phase of the wax to a state which solidified a larger percentage of its mass in the polymorphic β form. In FIG. 4 the lower melting point polymorphic α form has a peak centered at approximately 61° C., while the higher melting point polymorphic β form has a peak centered at approximately 79° C. The piston applied a maximum pressure to the wax of approximately 4400 pounds/inch$^2$ during the stroke cycles.

Figure 5:
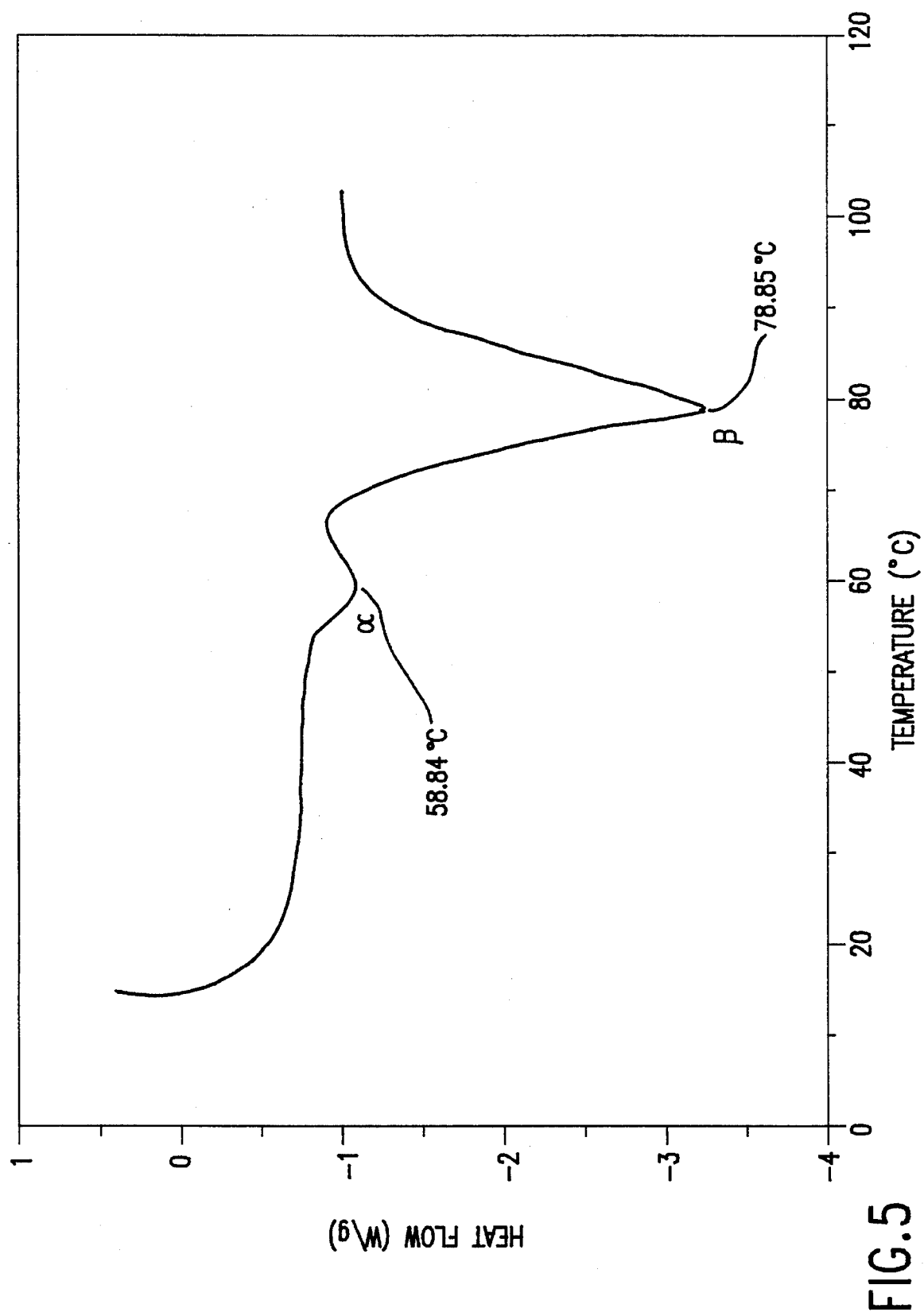
FIG. 5 is a DSC spectrum of glyceryl tristerate which has been melted to 90° C., subjected to the force of twenty piston stroke cycles, and resolidified.

FIG. 5 is a DSC spectrum of solidified tristearin which, while in the molten phase at 90° C., was subjected to the force of twenty compression/expansion cycles of a piston stroke before solidification. For this sample, the lower melting point polymorphic α form shows a peak centered at approximately 59° C., while the higher melting point polymorphic β form has a peak centered at approximately 79° C. Comparison of the ratios of the peak heights of FIG. 4 and FIG. 5 suggests that not much more of the molten wax was transformed into a state which would crystallize in the β polymorphic form by twenty stroke cycles than was accomplished by five stroke cycles of the piston. The piston applied a maximum pressure to the wax of approximately 4400 pounds/inch$^2$ during the stroke cycles.

However, it is quite evident when either the DSC spectra of FIG. 4 or FIG. 5 is compared to the DSC spectra of FIG. 3 that the force provided by additional piston stroke cycles transforms a larger fraction of the molten wax to a state which will solidify as the β polymorph than will solidify as the α polymorph.

Figure 6:
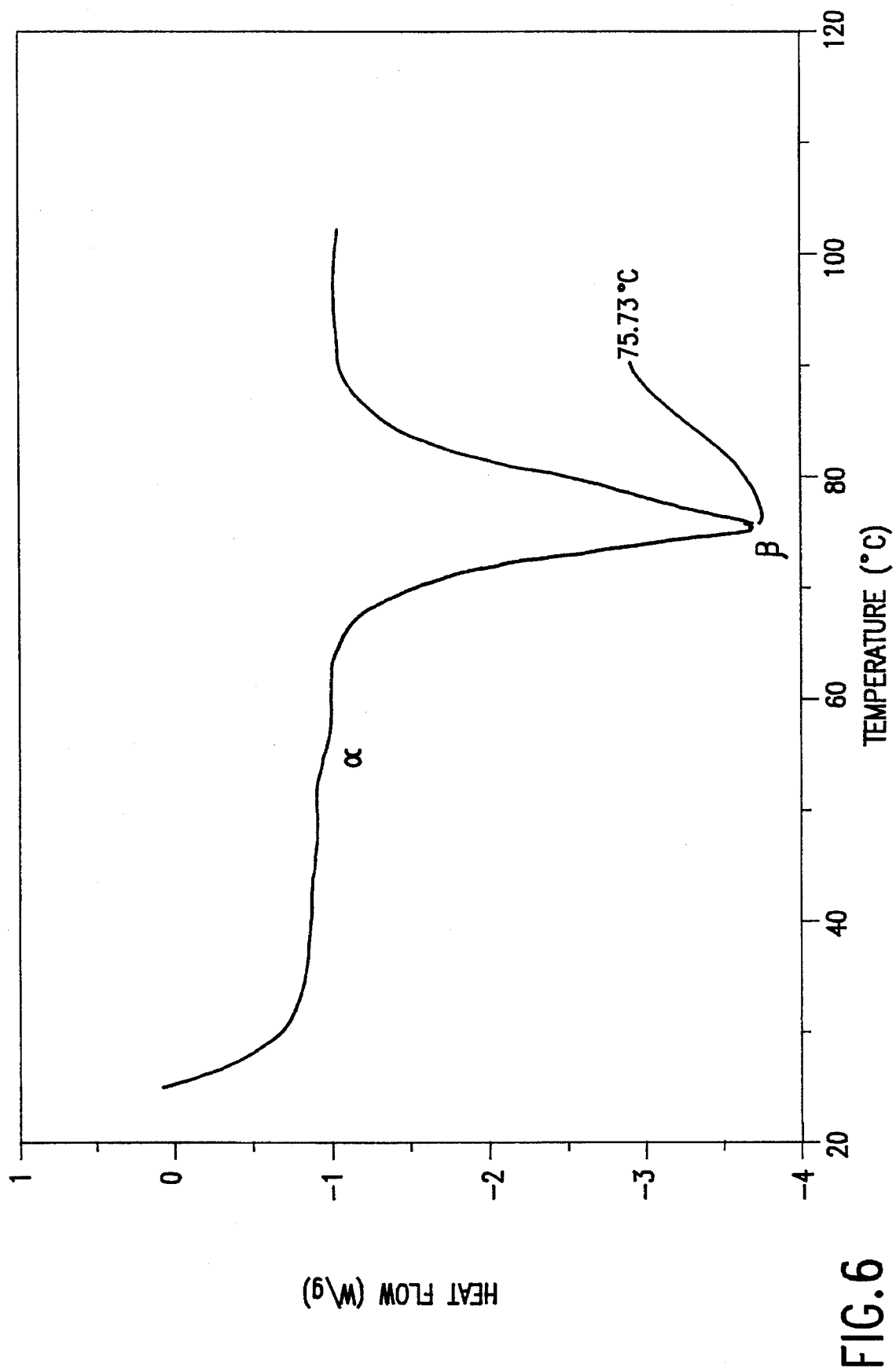
FIG. 6 is a DSC spectrum of glyceryl tristerate which has been melted to 145° C., subjected to the force of one piston stroke cycle, and resolidified.

FIG. 6 is the DSC spectrum of solidified tristearin which, while in the molten phase at 145° C., was subjected to the force of one compression/expansion cycle of the piston stroke before solidification. The very small endothermic peak centered at approximately 60° C. suggests that some residual polymorphic α form is still present. However, the relative magnitude of the larger polymorphic β peak centered at approximately 76° C. demonstrates that the transformed tristearin has solidified predominantly in the polymorphic β form. The piston applied a pressure to the wax of about 4400 pounds/inch$^2$ during the stroke cycle. The application of force clearly transformed the tristearin wax.

Figure 7:
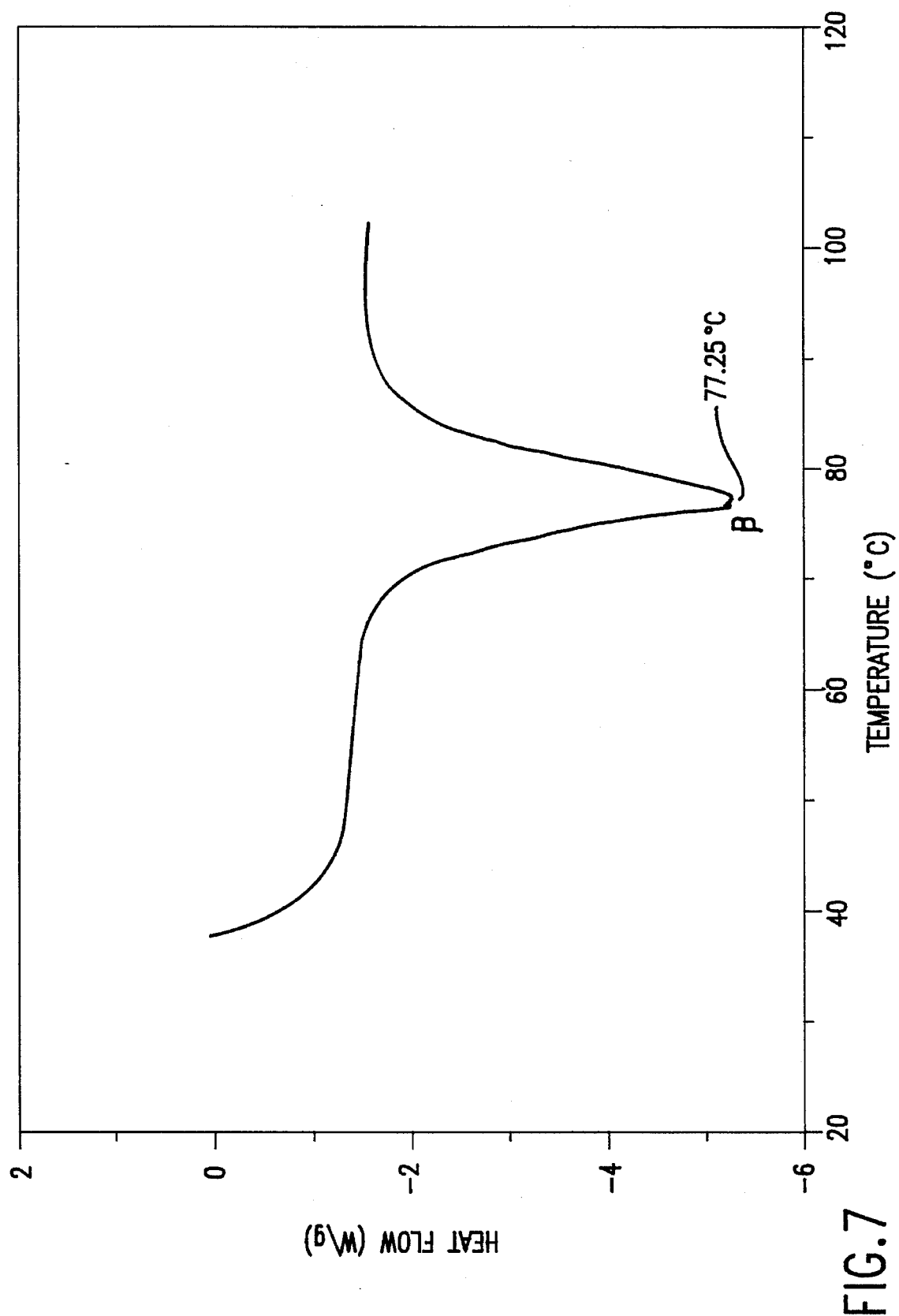
FIG. 7 is a DSC spectrum of glyceryl tristerate which has been melted to 145° C., subjected to the force of five piston stroke cycles, and resolidified.

FIG. 7 is the DSC spectrum of solidified tristearin which, while in the molten phase at 145° C., was subjected to the force of five compression/expansion cycles of a piston stroke before solidification. The presence of a single peak centered at approximately 77° C. clearly shows that the transformed tristearin has solidified in only the polymorphic β form. There is no indication of any residual polymorphic α form present. The piston applied a pressure to the wax of about 5500 pounds/inch$^2$ during each stroke cycle. In this case, the application of force has completely transformed a wax material, tristearin, which normally upon resolidification would crystallize in both the polymorphic α and β forms, to a state which upon resolidification now crystallizes in only the higher melting point polymorphic β form. This result is totally unexpected and unanticipated in the prior art.

Figure 8:
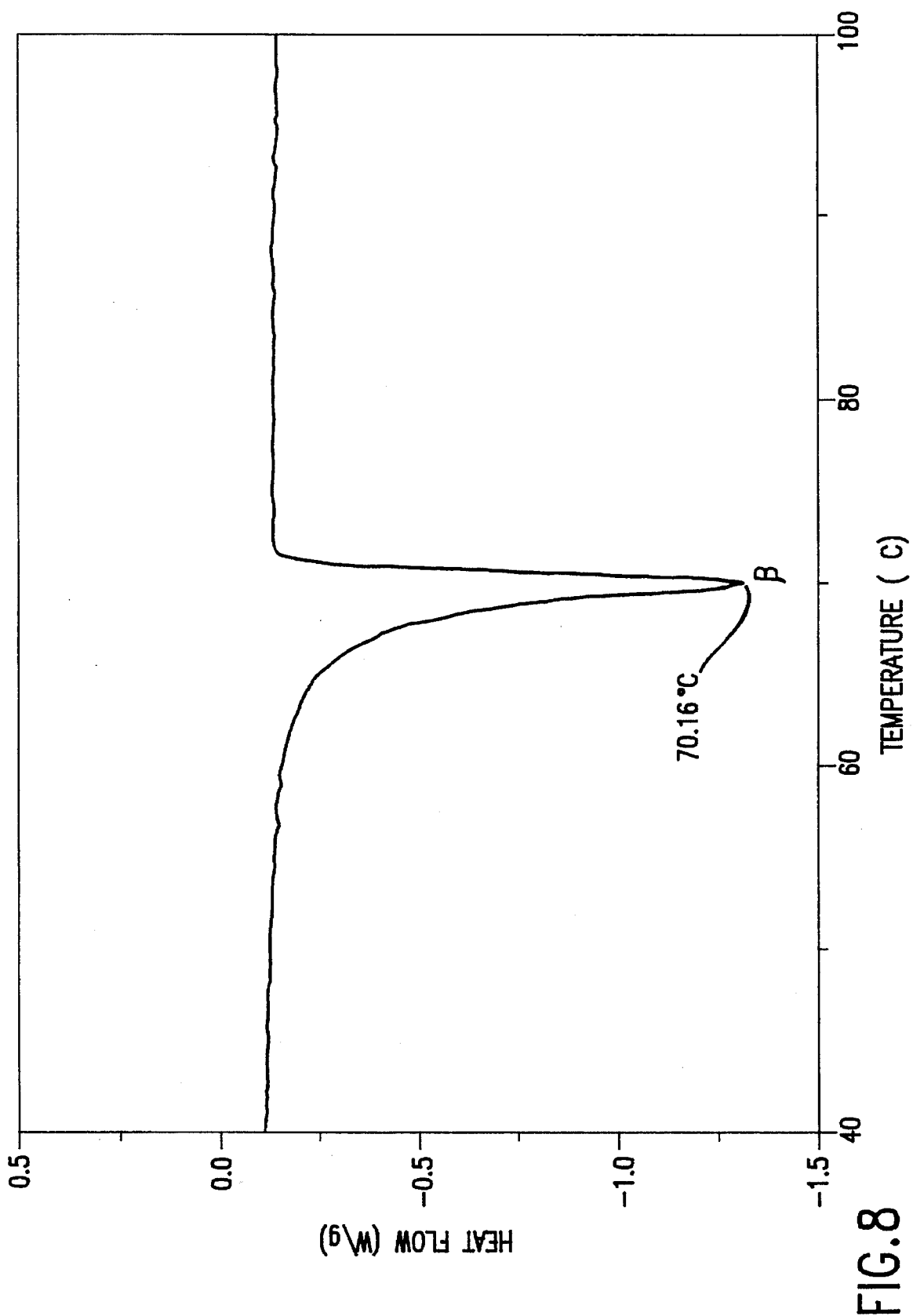
FIG. 8 is a DSC spectrum of glyceryl tristerate which has been melted to 120° C., subjected to the force of one piston stroke cycle, and resolidified.

FIG. 8 is the DSC spectrum of solidified tristearin which, while in the molten phase at 120° C., was subjected to the force of one compression/expansion cycle of a piston stroke before solidification. The piston applied a maximum pressure to the wax of approximately 9360 pounds/inch$^2$ during its stroke cycle. In FIG. 8 the peak centered at approximately 70° C. corresponds to the polymorphic β form. FIG. 8 clearly demonstrates that transformation of the melted wax to a state which solidifies only in the higher melting point β polymorph can be achieved with the force applied by a single stroke cycle of the piston. The transformation of the wax seems to depend on two factors: 1) the temperature of the liquid wax when force is applied; and 2) the total force applied to the molten wax.

Figure 9:
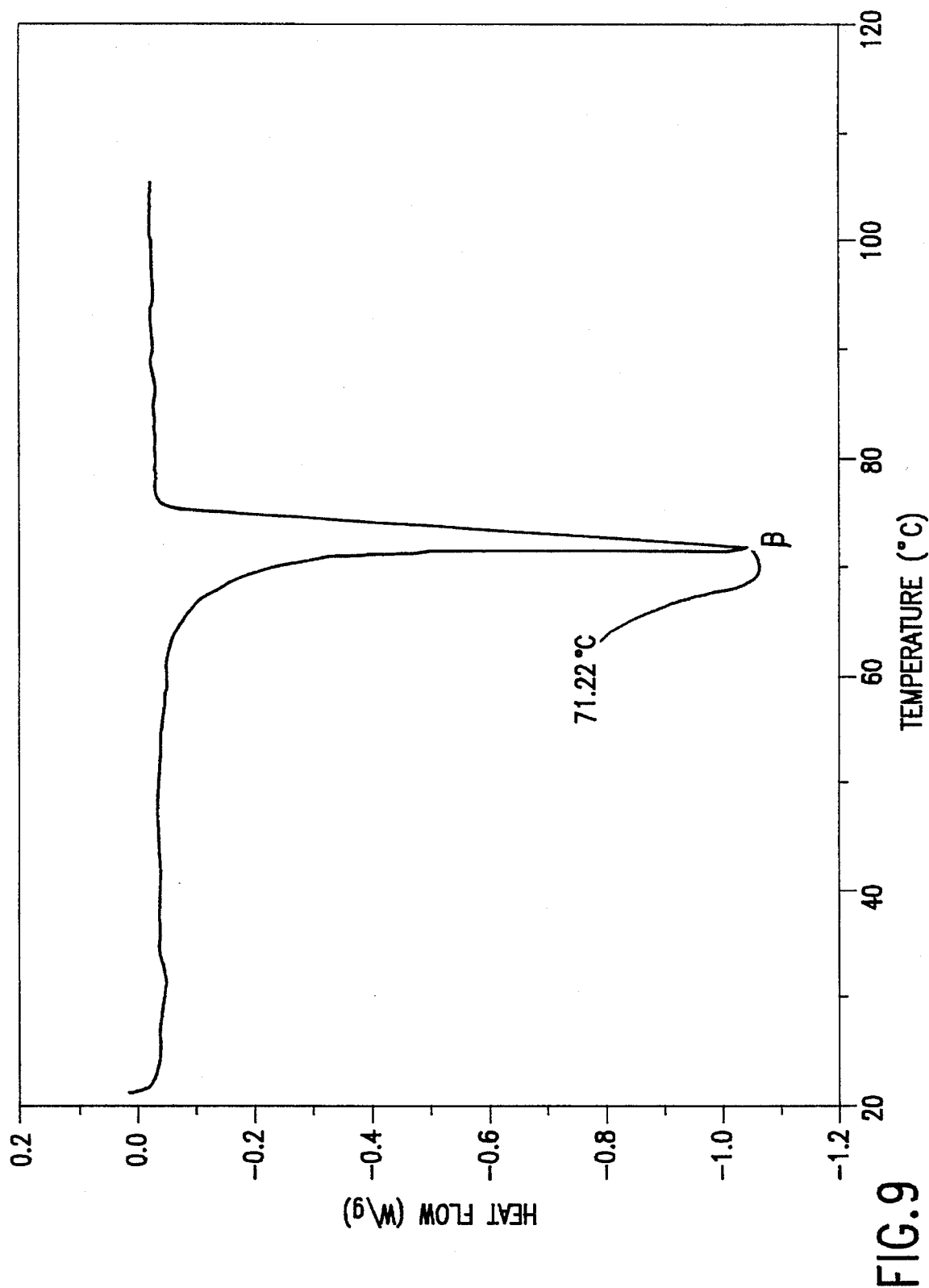
FIG. 9 is a DSC spectrum of glyceryl tristerate which has been melted, subjected to the force of ultrasound, and resolidified.

FIG. 9 is a DSC spectrum of solidified ultrasonically transformed tristearin. The tristearin was melted, heated to 90° C., and subjected for a period of ten minutes, while being stirred, to the force of ultrasound at an intensity level of 25 watts/cm$^2$. As can be seen from FIG. 9, upon resolidification, the ultrasonically transformed tristearin wax hardened entirely in the polymorphic β form yielding the customary β form peak centered at approximately 71° C. However, it should be noted that the time needed to transform the tristearin wax to the all β form by means of piston stroke cycles required only a few seconds, while the ultrasonic transformation required ten minutes. However, it is possible that either a greater total force applied by a higher power ultrasonic transducer or a different transducer geometry, cavity shape, or exposure area (such as in a flow cell) may effect the transformation in less time that the device presently available to Applicant.

In the above examples, a force applied to the molten wax transformed the wax to a different state. An example of an apparatus for producing the transforming force is shown schematically in FIG. 10. The apparatus is comprised of a reservoir 1 having a stirrer 11 located so as to stir the wax contents 3 of reservoir 1. Reservoir 1 is heated, if necessary, by heating coils 2, and the temperature of the wax material 3 within reservoir 1 is determined by temperature measuring apparatus 18. The wax may be charged to the reservoir in solid form and then melted to a molten liquid state or, alternatively, may be charged to the vessel in its molten form. A transfer conduit 14 leads to piston assembly 13. Piston assembly 13 consists of chamber 15, having inlet valve 6 and outlet valve 7 at opposite ends, to which is connected piston housing 4 which has within it movable piston 5. Movable piston 5 is displaced within housing 4 by motor 16. Motor 16 may be hydraulic, air, or electrically powered. Valves 6 and 7 may be solenoid valves, manually operated valves, or automatic check valves. Output transfer conduit 17 is connected to piston assembly 13 at exit valve 7 and leads to either a mixing or storage container (not shown). Transfer conduit 14 leading to piston assembly 13, piston chamber 15, and transfer conduit 17 leading from piston assembly 13 may be heated, if necessary, with heating coil 12 to maintain the temperature of the wax material 3 as it passes to, through, and from piston assembly 13. The mixing or storage containers (not shown) may be heated, if necessary, to maintain the temperature of the transformed wax material.

To prepare waxes for transformation the liquid wax is stirred by stirrer 11 until it has a uniform temperature (10 degrees above its melt point) as measured by temperature measuring apparatus 18. In the preferred embodiment, reservoir 1 is located above piston assembly 13 so that liquid wax 3 is gravitationally fed to piston assembly 13. Liquid wax 3 is admitted to chamber 15 where, after the valves seal off chamber 15, it is subjected to force as piston 5 is driven by motor 16 through its positive and negative displacement cycle within housing 4. The liquid wax 3 is shown under pressure in chamber 15 as wax 8. After admitting liquid wax 3, valves 6 and 7 may be closed while the piston cycles, subjecting the liquid wax to force by alternately applying and relieving pressure on the wax within closed chamber 15. Alternatively, the valve action may be adjusted to provide a semi-continuous flow of liquid wax through chamber 15. This can be accomplished by using check valves for both inlet valve 6 and outlet valve 7. As the piston is raised, the pressure within chamber 15 drops below the outside ambient pressure. Check valve 7 prevents previously transformed material from reentering chamber 15 while check valve 6 permits a quantity of liquid wax 3 to be drawn into chamber 15. As piston 5 begins the downward half of its stroke cycle, both check valves 6 and 7 close for a period of time allowing pressure to build up within chamber 15. At some point the pressure on liquid wax 3 exceeds the pressure setting of check valve 7 which then opens, permitting the transformed wax to flow out of chamber 15 into transfer conduit 17. The treated wax material may be collected in a heated container to maintain the temperature of the material or it may be cooled for storage purposes.

As shown earlier with reference to FIG. 7, complete transformation of molten tristearin at 145° C. to a liquid state which will solidify substantially in the all β polymorphic form is achieved after five repetitive stroke cycles of piston 5, each compression yielding approximately 5500 pounds/in$^2$ chamber pressure. Typically, only a couple of seconds are required to transform the wax material in this manner. Thus, the throughput of transformed wax is very high even for a small chamber. In the preferred embodiment the piston apparatus, piston assembly 13 consists of an air driven hydraulic pump such as that manufactured by S.C. Hydraulic Engineering Corporation, Model No. SC- 10-600-8. In such a pump, the force exerted by the piston on the liquid wax material within the chamber can be regulated by the choice of air pressure supplied to the motor. For the Model SC-10-600-8 pump, a minimum of approximately 35 pounds/inch$^2$ inlet pressure is required to activate the pump. Typical inlet pressure ranges to the pump which were found to produce sufficient force vary from 40 to 60 pounds/inch$^2$ of pressure. These inlet pressures result in pressures in the chamber of approximately 4400 to 6600 pounds/inch$^2$ since the pump has a hydraulic pressure multiplying effect of approximately 110. Chamber pressures as high as approximately 9360 pounds/inch$^2$ have been used with other pumps to successfully transform the waxes.

The transformed wax material 19 may either be collected for later use in a storage container heated, if necessary, to keep the material in the liquid phase or may be immediately used.

Figure 11:
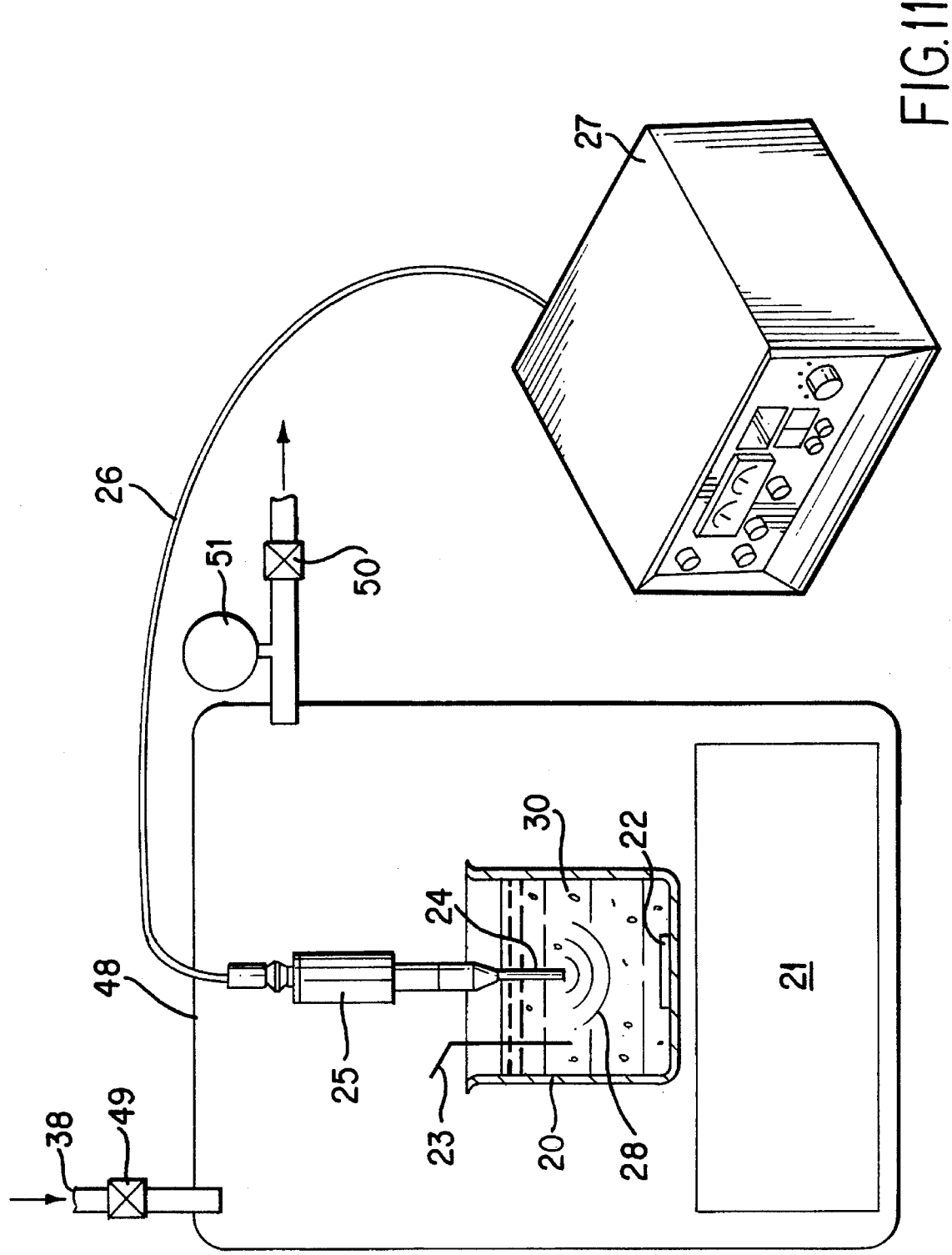
FIG. 11 is a perspective view of an enclosed ultrasonic homogenizer apparatus which produces the force necessary to transform waxes and entrap liquids therein.

An example of a second apparatus for producing the transforming force is shown in FIG. 11. A treatment container 20 may be heated, if necessary, by heater/stirrer 21 which is a combination heating element and magnetic stirrer. The native wax 30 which is to be transformed, in either liquid or solid phase is placed in container 20. If necessary, wax 30 may be heated by heater/stirrer 21 while being stirred by magnetic bar stirrer 22 driven by heater/stirrer 21 and brought to a uniform temperature as determined by temperature measuring apparatus 23. After the wax 30 has reached the desired uniform temperature, horn 24 of ultrasonic converter 25 is placed into the liquid wax 30. Converter 25 is connected by cable 26 to ultrasonic generator power supply 27. Ultrasound 28 is applied to liquid wax 30, once again resulting in transformation of liquid wax 30 into a liquid state of the wax which solidifies to a physically distinguishable form. For tristearin, a temperature of 90° to 145° C. is used. Typically, molten tristearin is subjected to the force of the ultrasound for a period of ten minutes at an intensity level of 25 watts/cm$^2$. Stirring is continued during the application of the ultrasound to ensure exposure of all the molten tristearin to the ultrasound. Once the transformation is complete, the transformed molten tristearin may be stored in a heated container or used immediately.

Figure 10:
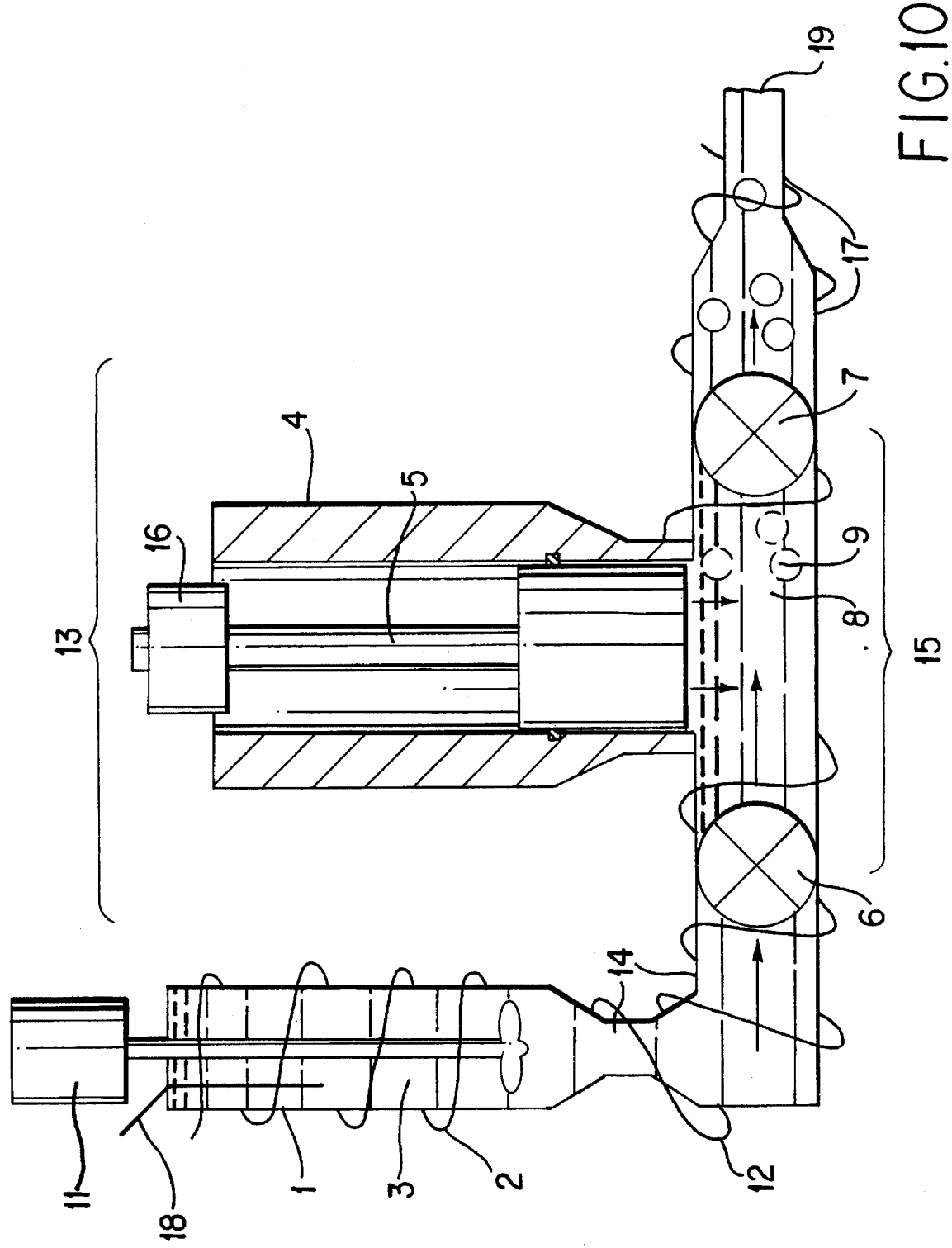
FIG. 10 is a schematic representation of a piston apparatus used to produce the force necessary to transform waxes and entrap liquids therein.

Several possible physical mechanisms may account for the transformation of the waxes by the applied force. For those polymorphic waxes, such as tristearin, which convert to a molten state which hardens in the stable higher melting point β polymorph, a possible mechanism may be that at the high pressure achieved as the piston is forced against the molten wax within chamber 15, the molten wax begins to crystallize in the β form. These initial β form crystals 9 are indicated in FIG. 10 within a pressurized liquid wax 8. Upon leaving chamber 15 the β form crystals 10 would serve as nucleation centers for further ordering of the molecules so that, as the wax solidified, it would crystallize principally in the polymorphic β form. By this mechanism, more β form crystals 10 are created by each successive application of force by the piston stroke cycles, thereby creating a larger number of β form nucleation centers. At some point the concentration of β form nucleation centers 10 would be sufficient to cause the solidification of the liquid wax completely in the polymorphic β form. Applicant, however, does not rule out as a possible mechanism the alternative possibility that it is the release of pressure either during the piston's negative displacement or by release of the pressurized wax through the check valve which initiates β form crystal formation.

On the other hand, the force may work through means other than pressure to transform the waxes. That some other mechanism is at work is suggested by the fact that the force generated by ultrasound also transforms the molten waxes. Ultrasound is usually considered to work its effects through the creation of cavitation bubbles in the medium, although pre-cavitation oscillation of the medium occurs. The collapse of cavitation bubbles is accompanied by localized shock waves, shear forces, and abrupt temperature spikes. Perhaps it is the force applied by shear, shock wave, or heating produced by either the piston cycle or ultrasound that transforms the waxes. Applicant has discovered the effect but does not know the mechanism.

It is now clear that waxes can be transformed into more stable crystalline structures through the pressure process techniques described above. In order to gain further appreciation for the nature of these transformations, reference is now made to FIGS. 12A–C wherein the alpha, alpha/beta and beta crystalline structures of a polymorphic wax are illustrated.

Figure 12A:
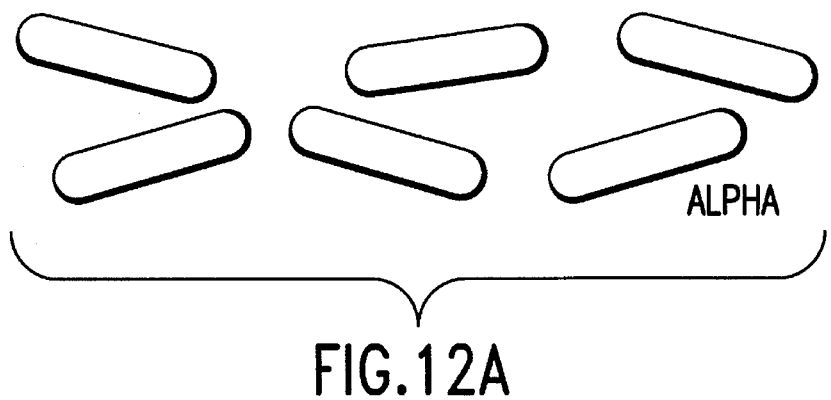
FIGS. 12A–12C illustrate the various crystalline structures of a polymorphic wax or other polymorphic substance.
Figure 12B:
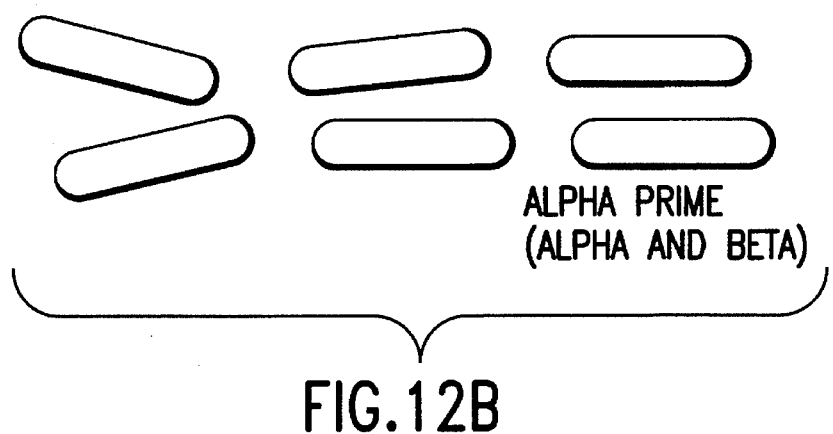
Figure 12C:
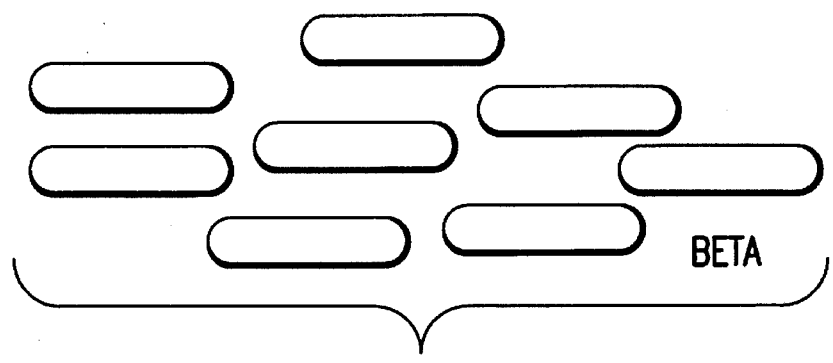

FIG. 12A depicts the alpha polymorphic structure characterized by a disorganized crystalline lattice. This structure is generally physically unstable and is, therefore, a poor host for liquid entrapment. As observed above, the DSC spectra of such a structure typically exhibits a lower melt point than the alpha prime and beta configurations. FIG. 12B depicts partial alignment of the crystal lattice. This intermediate structure, commonly referred to as alpha prime, has greater stability than the alpha lattice. Finally, FIG. 12C depicts the most stable, beta crystalline lattice which, as evidenced below, affords the greatest protection to liquids entrapped within it. The beta form exhibits the highest melt point on a DSC spectra.

Figure 13:
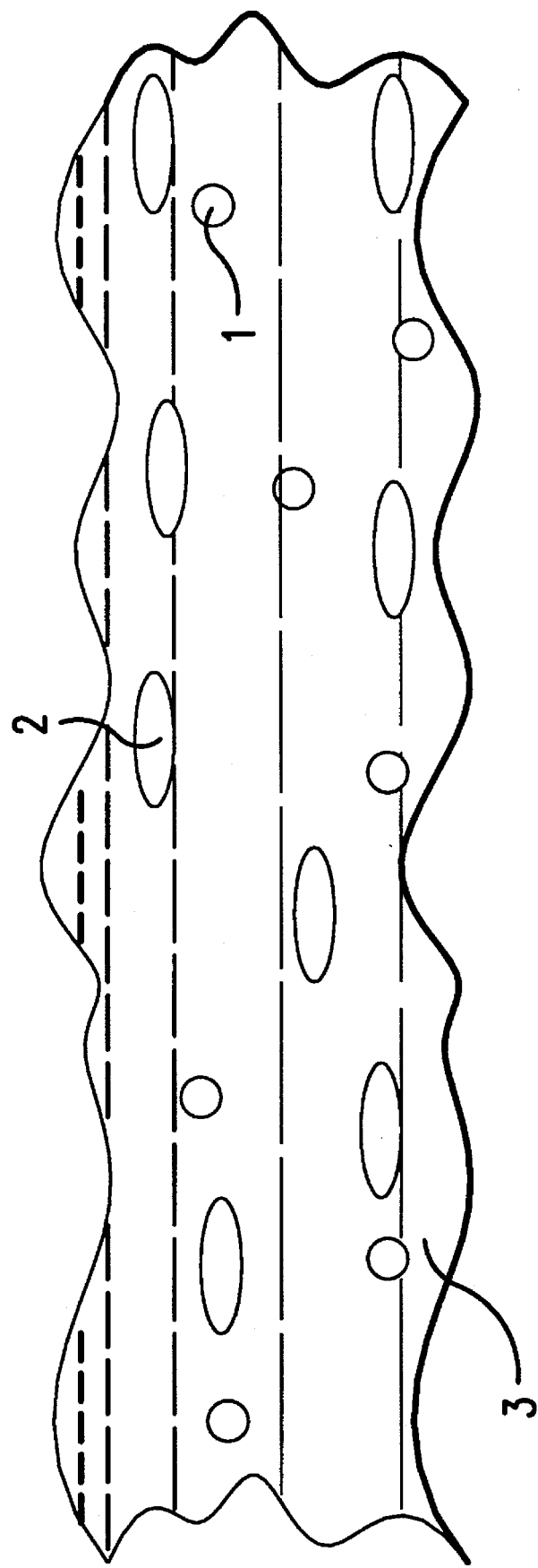
FIG. 13 is an illustration of the product produced by the various pressure treatment processes, wherein liquid droplets are entrapped and dispersed within a wax host substrate.

Applicant has discovered that liquids may be entrapped within the more stable matrix of the beta polymorph with minimal vaporization losses using the processes described above. Further, in many cases, the resultant end-product itself is more resistant to the effects of oxidation, reduction, volatilization and other unwanted effects on the entrapped liquids. FIG. 13 illustrates the structure and composition of the end-product, wherein entrapped droplets of liquid 1 are interdispersed within the crystal lattice 2 of a host fat or wax 3.

Examples of liquids which may be successfully entrapped within transformed waxes by the subject methods are listed in Table 2, below. It should be understood that the list is meant to be merely illustrative and is not intended to limit the scope of the invention as defined in the appendant claims.

TABLE 2

| LIQUIDS USABLE AS ENTRAPPED COMPOUNDS | |
| --- | --- |
| Choline Liquid | Solvents |
| Liquefied Vitamins | Water |
| Flavor Oils | Fragrance Oils |
| Methione Liquid | Lysine Liquid |
| Liquid Catalysts | Fire Retardant Liquids |
| Bleach Formulations | Cleaning Solutions |

*Any other liquid including those in mixture, melt, slurry, solution, suspension, emulsion, or dispersion.

A conventional method of entrapping liquids in a wax material involves mixing the liquid in a molten form of the wax and then allowing the wax to slowly cool until it is re-solidified. In Experiment 1, below, an open bowl planetary mixer (not shown) manufactured by Hobart Inc. was employed to entrap liquids according to this method for the purpose of comparing attendant liquid loss with that experienced by the subject methods. It is noted summarily that when the open bowl approach is used with volatile liquids, a large percentage of the liquid, as measured by weight, will evaporate upon contact with the molten host wax before re-solidification and full entrapment can occur.

EXPERIMENT 1: OPEN BOWL MIXER METHOD 1. 200 g of a vegetable triglercide fat known as Dynasan 118, supplied by Huls American Corp., was heated to 80° C. in a beaker on a hot plate until molten.

2. An open bowl mixer, supplied by Hobart Corp., using an anchor type blade is then heated by a heating mantle placed under the bowl to a jacket temperature of 90° C. throughout.

3. The mixer is NOT enclosed.

4. The molten Dynasan is delivered to the heated open mixer and agitated slowly. The temperature of the molten fat is monitored to maintain the fat in a molten state. The temperature of the molten fat is kept at least 10° C. above the melt point of the fat. Dynasan 118 has a melt point of 72° C. and is, therefore, maintained at 82° C., for 15 minutes while stirring.

5. 50 g of Orange Flavor Oil, supplied by Prima Food International Corp., is then added to the molten fat in the mixer and stirred under mild agitation for 15 minutes while maintaining the heat to the melt point of the fat, at least 72° C.

6. After 15 minutes heat is reduced and the mix allowed to cool to ambient temperature while stirring.

7. After one hour the mixer is stopped and the product inspected.

RESULTS

Product: A pale yellow powder with entrapped flavor liquid. The total yield was 90.8% (227 g) from a 250 g starting run. The loss, 9.2% (23 g) of total weight is attributed to volatilization of the liquid component, assuming that all of the wax was recovered. Flavor loss was calculated as follows:

23 g. loss/50 g. initial flavor loading= 46% loss

In the above example it can be clearly seen that while some of the flavor oil liquid has been entrapped, a high loss was encountered during processing. Other prior art methods suggest the use of combining volatile liquids with lipoidal materials under superatmospheric conditions to reduce such losses. The following method is illustrative.

Pressurized Mixer Process

STEP 1: Wax or fat is reduced to a molten state by melting the material in an enclosed vessel by heating the wax under mild agitation.

STEP 2: The liquid is then added to the molten wax in an enclosed mixer vessel under mild agitation.

STEP 3: Without exposing the mixture to an open environment, the molten wax/liquid mixture is then delivered to a pressurized mixer device, wherein the pressure within the chamber is increased to a point higher than the vaporization pressure of the liquid.

STEP 4: The pressure treated molten mixture is maintained in the pressurized mixer where the mixture is allowed to cool gradually under agitation. Eventually the wax re-solidifies and continued agitation (granulation) results in a fine powder.

Figure 14A:
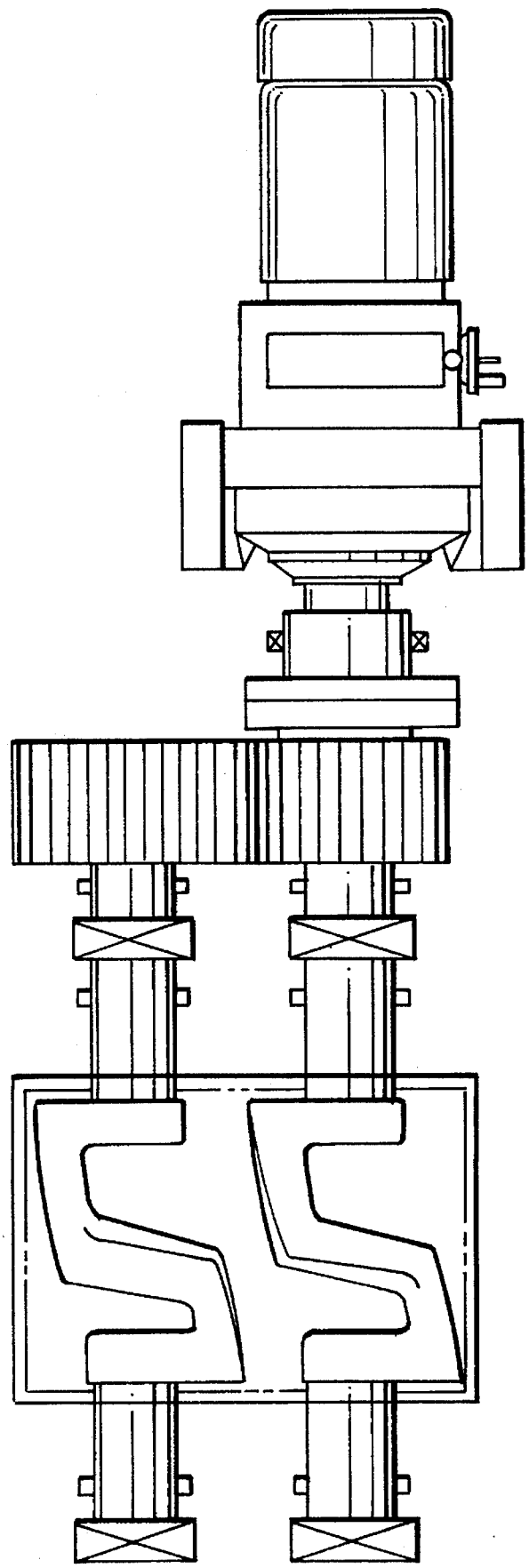
FIG. 14A is a schematic of a pressurized Sigma Mixer.
Figure 14B:
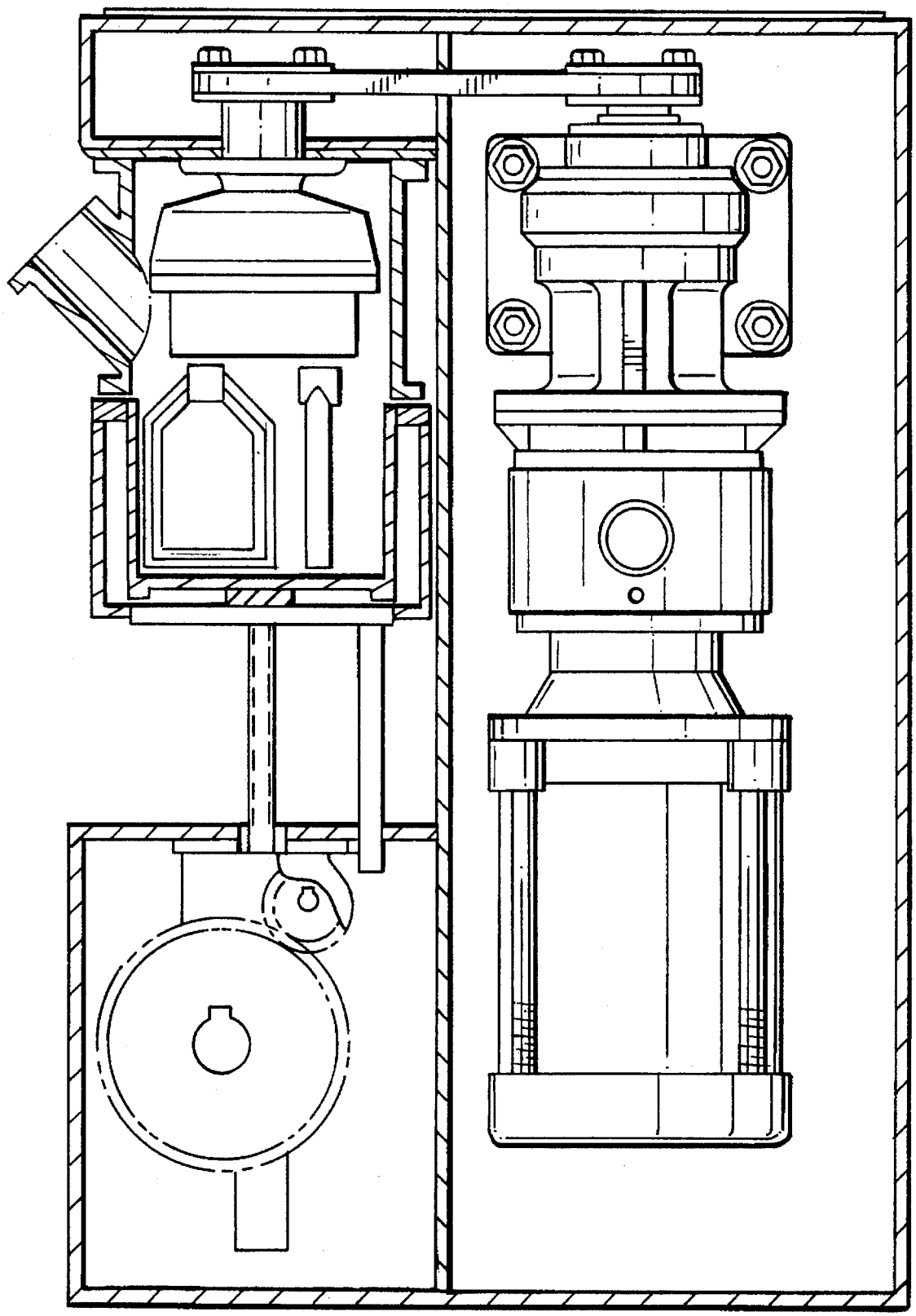
FIG. 14B is a schematic of a pressurized Planetary Mixer.
Figure 14C:
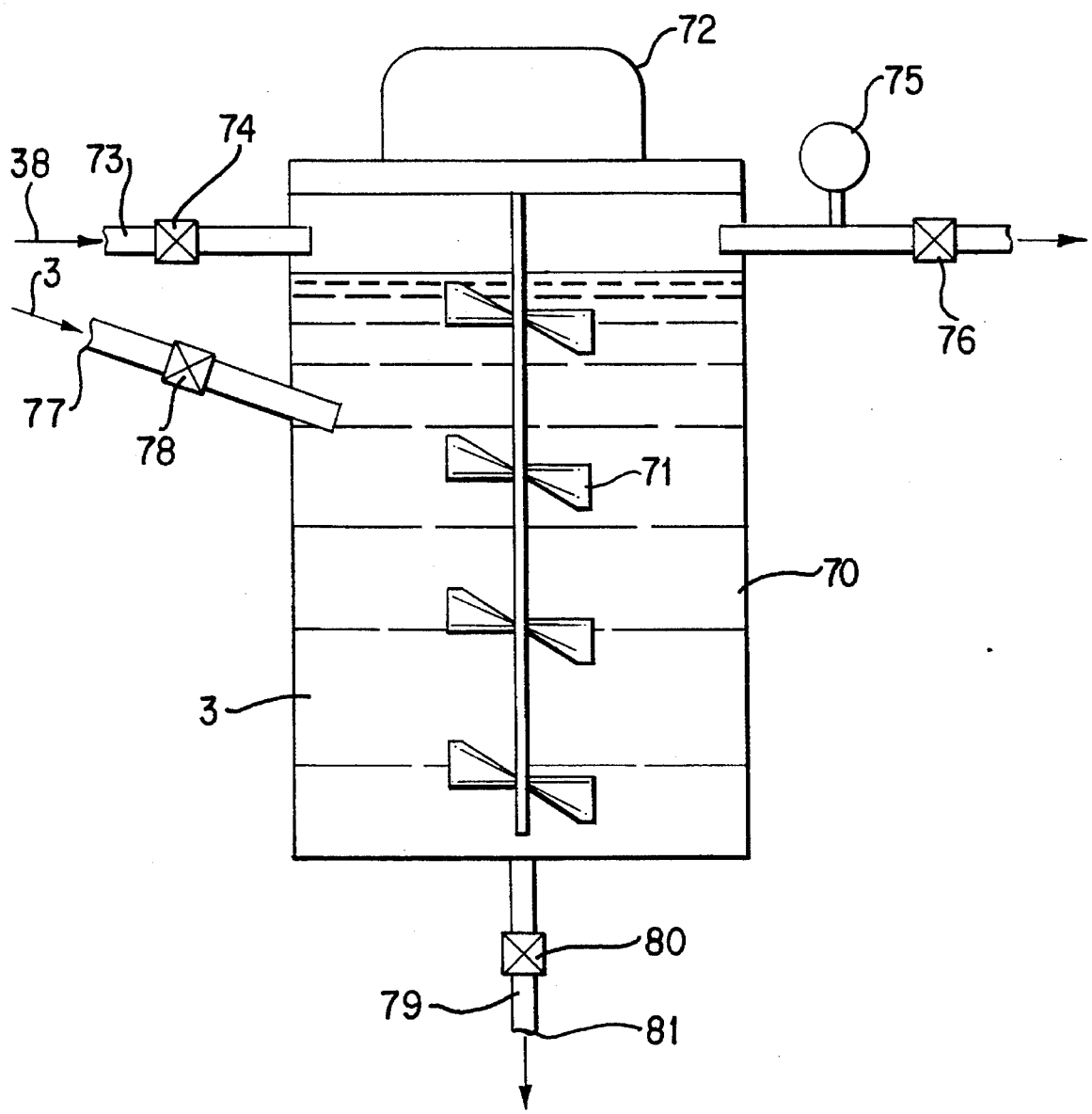
FIG. 14C is a schematic of a pressurized Mixer Cell device.

Mixing devices suitable for this process include a pressurized Sigma Mixer (FIG. 14A), a pressurized planetary mixer (FIG. 14B), or a pressurized mixer cell device (FIG. 14C). While these devices are capable of successfully reducing liquid losses during processing, the are less efficient than the subject pressure processing techniques described earlier and are incapable of producing a transformed polymorphic wax which maintains its beta configuration upon subsequent melting and re-solidification. Realization of more efficient entrapment and a stable end-product may be accomplished by the piston pressurization apparatus depicted in FIG. 10 in accordance with the following method:

STEP 1: Reduce the wax or fat to a molten state by heating the material in an enclosed vessel under mild agitation.

STEP 2: Charge the liquid to the molten wax in an enclosed vessel under mild agitation.

STEP 3: Without exposing the mixture to an open environment, the molten wax/liquid material is then charged to the apparatus of FIG. 10, and subjected to either a single pressure stroke or to multiple pressure strokes of the piston pressure applicator.

STEP 4: The pressure treated molten material may then be optionally delivered to a pressurized mixer where the mixture is allowed to cool gradually under agitation and re-solidify into a fine powder. The result is the entrapped liquid product illustrated in FIG. 13.

Additionally, the piston pressurization process may be combined with the foregoing pressurized mixer technique to achieve superior entrapment results.

EXPERIMENT 2: PISTON PRESSURIZATION WITH PRESSURIZED MIXER 1. 200 g of a vegetable trigliceride known as Dynasan 118, supplied by Huls America Corp., was heated to 80° C. in a beaker on a hot plate until molten.

2. A Sigma mixer, using an S type blade is then heated to a jacket temperature of 90° C. throughout.

3. The Sigma is enclosed by locking the lid to the mixer chamber in place.

4. Raise the pressure within the mixer chamber to 10 psig by placing compressed air into the Sigma system.

5. The apparatus of FIG. 10 was pre-heated to 90° C.

6. The molten fat was then passed through the apparatus, which was set at 90 psi inlet pressure, speed level 3. The subject apparatus, also known as a Beta Processor or Beta System, pressure treats the molten fat using a single stroke of the piston for the purpose of causing an alignment of the crystalline structure of the fat upon re-solidification. The molten wax is passed through the machine only once.

7. The molten wax is delivered to the heated Sigma Mixer and agitated slowly. The temperature of the wax is checked to maintain it in a molten state. The temperature of the molten wax is kept at least 10° C. above the melt point of the wax. Dynasan 118 has a melt point of 72° C. The Sigma mixer is, therefore, maintained at 82° C. for 15 minutes while stirring.

8. The heat is then reduced to allow the wax to cool to a temperature of 65° C. At this point the wax is still in a melted state.

9. At 65° C. add 50 g of orange flavor oil, supplied by Prima Food International Corp., to the cooled molten fat in the pressurized Sigma mixer and stir under mild agitation for 15 minutes while maintaining the heat at least 65° C.

10. After 15 minutes, deactivate the heat to the Sigma mixer. Allow the mix to cool to ambient temperature while stirring, but maintain the pressure in the mixer at 10 psig.

11. After one hour, release pressure in the mixer and inspect product. It

RESULTS

Product: pale yellow powder with entrapped flavors. The total yield was 98.5% (246.25 g) from a 250 g starting run. The loss is once again attributed to the volatilization of flavor material. Flavor loss was calculated as follows:

3.75 g. loss/50 g. initial flavor loading= 7.5% loss

Figure 15:
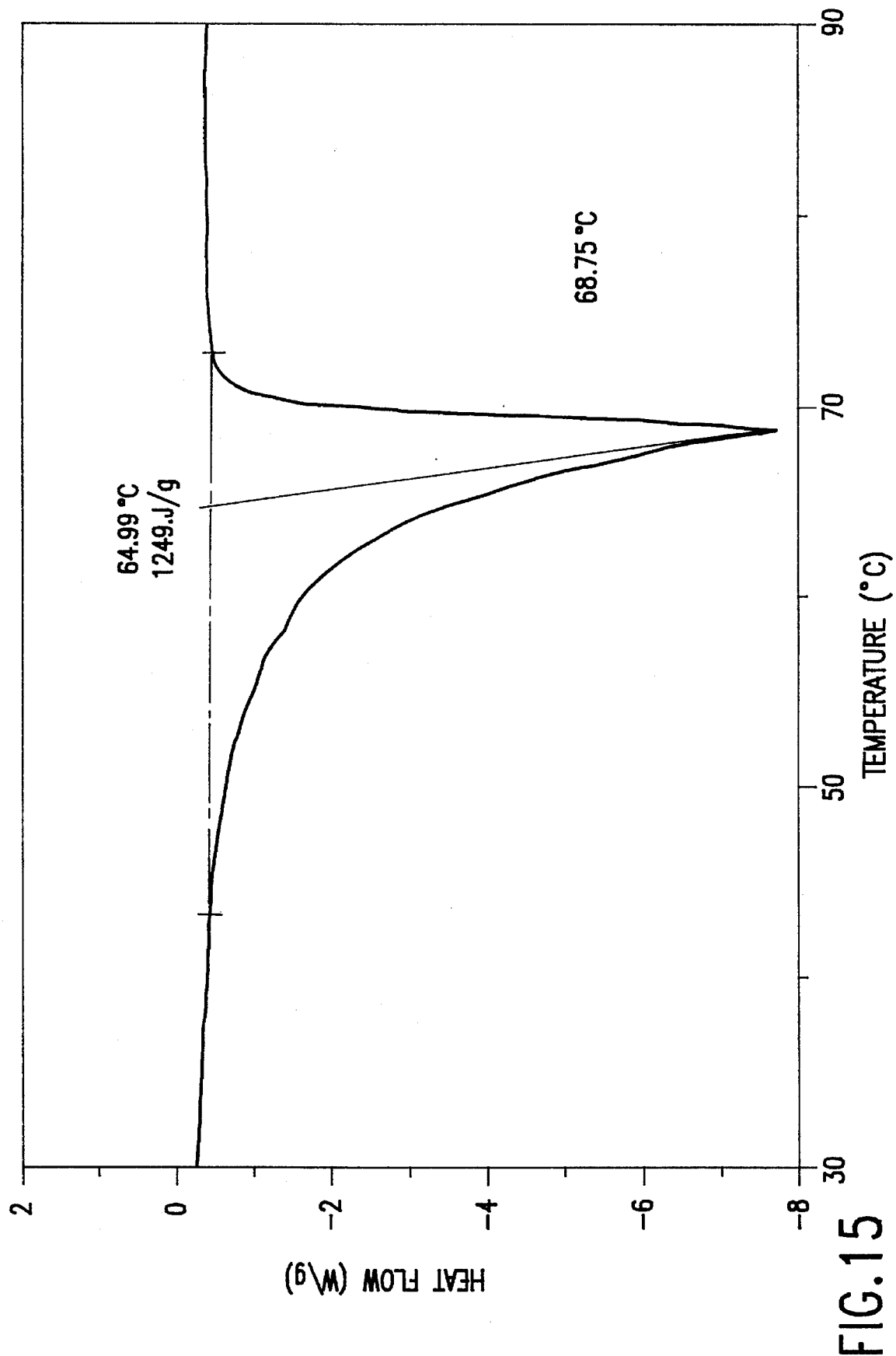
FIG. 15 is a DSC spectragraph of glyceryl tristerate melted to 90° C., subjected to the force of one piston stroke cycle, and combined under pressure with orange flavor oil.

The use of the Beta Processor and a pressurized mixer produces the highest yield of product; the lowest liquid volatilization. FIG. 15 shows the DSC spectra of the Beta treated wax/flavor oil product. Note that it clearly indicates a crystal structure which conforms to that of the most stable form of Dynasan 118 exhibiting no peak for the alpha polymorph. This indicates that the most stable crystalline lattice has been achieved upon resolidification which is characterized by far fewer microfissures in the wax host material. Such a structure offers improved resistance to vaporization, oxidation and reduction of the entrapped liquid.

In both instances of Experiment 1 and 2, a standard amount of the same flavor oil liquid was added to the wax host substrate, at 20% by weight. To explore whether higher loadings were possible in a pressurized system, the next experiment was conducted.

EXPERIMENT 3: PISTON PRESSURIZATION AND PRESSURIZED MIXER, HIGHER LOADING 1. 200 g of a vegetable trigliceride wax known as Dynasan 118, supplied by Huls America Corp., was heated to 80° C. in a beaker on a hot plate until molten.

2. A Sigma mixer, using an S type blade was then heated to a jacket temperature of 90° C. throughout.

3. The Sigma mixer was enclosed by locking the lid to the mixer chamber in place.

4. Pressure within the mixer chamber was raised to 10 psig by placing compressed air into the Sigma system.

5. A Beta processor with a "C" type baffled chamber was preheated to 90° C.

6. The molten wax was then passed through the Beta system, which was set at 90 psi inlet pressure, speed level 3. The Beta system pressure treated the molten wax using a single stroke of a piston for the purpose of causing an alignment of the crystalline lattice of the wax upon resolidification. The molten wax was passed through the machine only once.

The molten Dynasan was delivered to the heated Sigma mixer and agitated slowly. The temperature of the wax was observed to maintain it in a molten state. at 82° C. for 15 minutes, while stirring.

8. The heat was then reduced to allow the wax to cool to a temperature of 65° C. At this point, the fat was still in a melted state.

9. At 65° C., 100 g of orange flavor oil was added to the melt in the pressurized Sigma mixer and stirred under mild agitation for 15 minutes.

10. After 15 minutes, the heat was eliminated and the material permitted to cool to ambient temperature while stirring. Pressure in the mixer was maintained at 10 psig.

11. After one hour, pressure in the mixer was reduced to standard and the product was inspected.

RESULTS

Product: a pale yellow powder with entrapped flavors. The total yield was 98.0% (294 g) from a 300 g starting run. The loss is attributed to the volatilization of flavor material. Flavor loss was calculated as follows:

3.0 g. loss/100 g. initial flavor loading= 3% loss

The use of the piston pressurization process produced a transformed wax end-product which contains a higher content of the liquid material. The next group of experiments illustrate that active chemical compounds may be entrapped within the wax host through the processes of this invention.

Three examples are provided:
Choline Chloride Solution: This compound consists of 70% active
Choline in 30% water and is used as an example to illustrate an active liquid solution.
Dibutyl Tin Dilurate is a fully active catalyst liquid.
DD-8307 is a liquid paraffin formulation containing chlorine and bromide fire retardant compounds.
Choline is a vitamin complex supplied usually in a choline chloride or choline bitartrate form. The highest active ingredient form is choline chloride which possesses as much as 85% active choline compared to just 46% active choline in the bitartrate carrier form. Solid choline chloride is very hygroscopic and difficult to handle. A liquid form containing 70% active choline in 30% solution is available to reduce handling problems, but again this is in a liquid form and not very suitable to many applications. In the next experiment, entrapment of the choline active within a wax host is accomplished to provide a solid matrix end-product with less hygroscopicity.

EXPERIMENT 4: BETA SYSTEM WITH PRESSURIZED MIXER, CHOLINE LIQUID

All steps of Experiment 3, above, were carried out in an identical manner with the exception of step 9 wherein 50 g of a solution containing 30% water and 70% dissolved choline chloride, supplied by DuCoa Corp., was substituted for the flavor liquid.

RESULTS

Product: a white free flowing powder with entrapped deposited choline chloride. Inventor theorizes that water evaporated, leaving depositions of the choline chloride remaining within the fat host matrix. Although choline chloride in solution typically exhibits a strong fishy odor, this odor was not present in the final end product evidencing superior entrapment.

The total yield was 94.10% (235.25 g) from a 250 g starting run. The loss is attributed to the evaporation of the water component of the choline solution. With an initial liquid loading of 50 g, the total liquid loss was 14.75 g, or 29.5% of the starting composition by weight. As most of the core composition was water, it is believed that the water evaporated and that the remaining choline active ingredient was deposited in the fat matrix.

EXPERIMENT 5: BETA SYSTEM WITH PRESSURIZED MIXER, USING LIQUID CATALYST

All steps of Experiment 2, above, were carried out in an identical manner with the exception of step 9 wherein 50 g of a catalyst solution known as Dibutyl Tin Dilaurate, supplied by Air Products Corp. was substituted for the flavor liquid.

RESULTS

Product: a white free flowing powder with entrapped deposits of the catalyst compound within the fat matrix. The total yield was 96.75% (241.87 g) from a 250 g starting run. The loss was attributed to the partial evaporation of the catalyst solution. Liquid loss was calculated as follows:

8.13 g. loss/50 g. initial catalyst loading=16.3% loss

EXPERIMENT 6: BETA SYSTEM WITH PRESSURIZED MIXER, USING LIQUID FIRE RETARDANT FORMULATION

All steps of Experiment 2, above, were carried out in an identical manner with the exception of step 9 wherein 50 g of a fire retardant mixture known as DD-8307 supplied by Dover Chemicals Corp. was substituted for the flavor liquid.

RESULTS

Product: a free flowing powder with entrapped deposits of the fire retardant compound within the wax host matrix. The fire retardant liquid was a paraffin formulation consisting of bromide and choline components. The solid wax formulation melted at 70° C. and provided a stable entrapment for the fire retardant liquid, in a dry form capable of solid addition to urethane foam products. The total yield was 95.3% (238.25 g) from a 250 g starting run. Liquid loss was calculated as follows:
11.75 g. loss/50 g. initial fire retardant loading= 23.5% loss The above experiments clearly show that other liquids, and particularly those containing active compounds may successfully be entrapped within a transformed wax matrix through the subject piston pressurization process.

Figure 16:
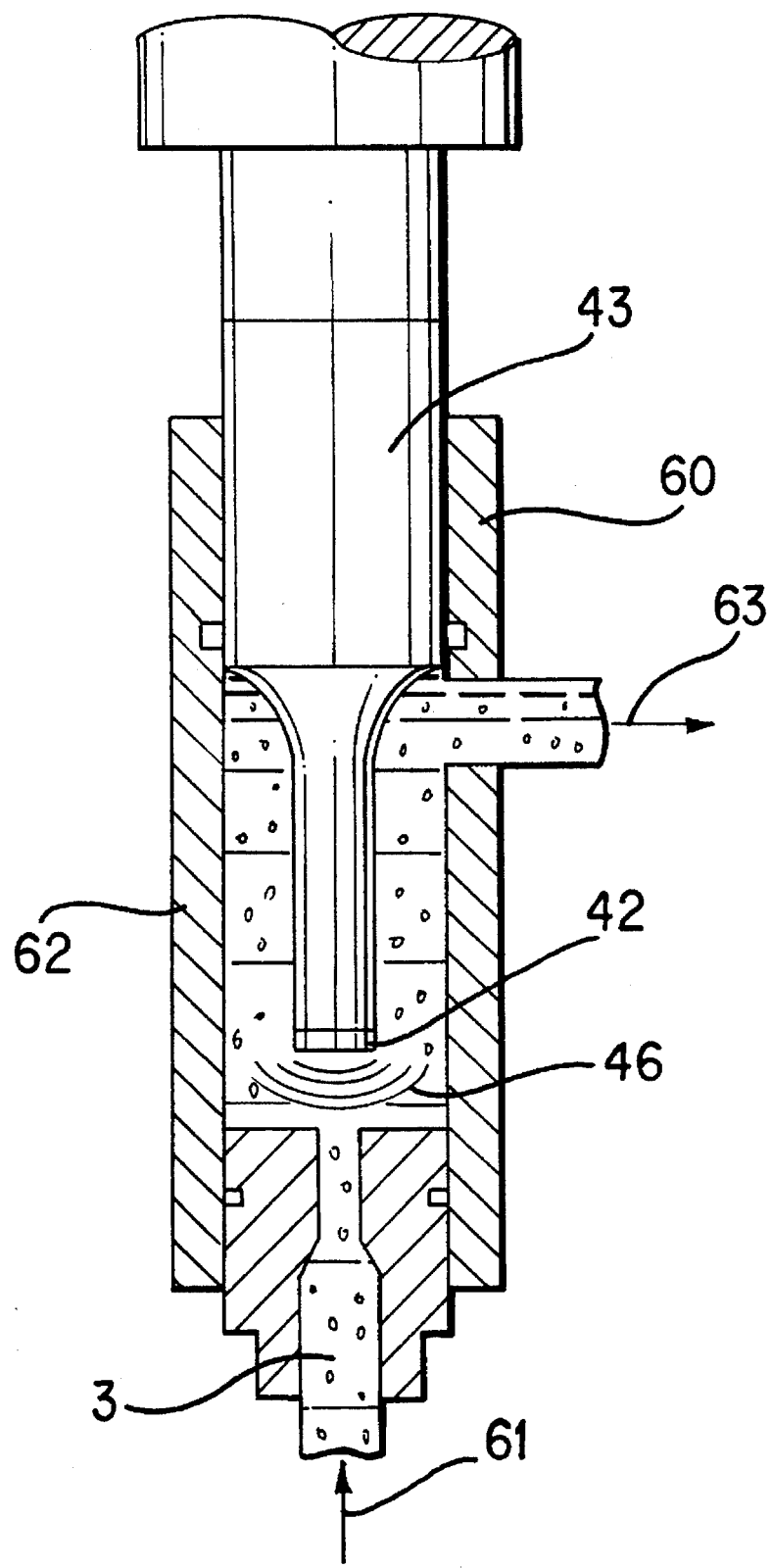
FIG. 16 is a schematic diagram of an ultrasonic flow cell apparatus used to entrap liquids within transformed waxes.

Applicant has also discovered the ultrasonic energies may be employed to achieve a highly stable beta state for waxes, as described above, and that liquids may be entrapped within the transformed waxes using either an enclosed ultrasonic flow cell as shown in FIG. 16, or the enclosed pressurized ultrasonic homogenizer system described earlier (FIG. 11 ). The method may be summarized as follows:

STEP 1: Wax or fat is reduced to a molten state by melting the material in an enclosed vessel by heating the wax under mild agitation.

STEP 2: The target liquid is then added to the molten wax in an enclosed vessel under mild agitation.

STEP 3: Without exposing the material to an open environment the molten wax/liquid is then delivered to an enclosed ultrasonic flow cell (FIG. 16) or an ultrasonic homogenizer system (FIG. 11) and subjected to treatment by the ultrasonic pressurization and cavitation energies.

STEP 4: The ultrasonically treated molten material may then optionally be delivered to a pressurized mixer where the mixture is allowed to cool gradually under agitation. Eventually the wax re-solidifies into a fine powder resulting in the liquid entrapped end-product illustrated in FIG. 13.

Reference is once again made to FIG. 11 wherein an enclosed ultrasonic homogenizer system is illustrated. When entrapment of liquids, rather than mere transformation of waxes is desired, an enclosure 48 encases the ultrasonic treatment system. Pressure is maintained within the enclosure 48 by allowing compressed air 38 to enter the enclosure and become sealed by locking valves 49 and 50. A pressure gauge 51 measures the pressure within the enclosure 48. At the completion of the processing, the pressure is released through outlet valve 50.

An alternative ultrasonic system is shown in FIG. 16, wherein a continuous ultrasonic flow cell device is employed. The ultrasonic tip is sealed by an enclosure 62. The molten wax/liquid 3 enters the flow cell housing 62 through the inlet channel 61 and flows past and around the tip 42 of the ultrasonic transducer 43. Ultrasound 46, emanating from the tip 42, treats the molten wax/liquid 3 with high intensity sound waves, producing a cavitation and heating effect within the wax/liquid 3. The treated molten wax exits the cell via outflow conduit 63. The cell is heated to keep the wax in a molten state.

Upon exiting the ultrasonic flow cell the treated molten wax/liquid may be optionally delivered to a pressurized mixer, where, upon cooling, it resolidifies into the most stable form or Beta state of the wax, thereby entrapping the liquid within its matrix.

Applicant theorizes that the cavitation energies produced by the ultrasonic transducer act to produce an energy transmission to the molten wax in much the same manner as developed by the pressure shock wave effect generated when the piston of the Beta device is applied. In each case, a polymorphic structural change results within the treated wax resulting in a more stable host for entrapped liquids.

EXPERIMENT 7: ULTRASONIC SYSTEM WITH PRESSURIZED MIXER, USING CHOLINE LIQUID 1. 200 g of a vegetable trigliceride fat known as Dynasan 118, supplied by Huls America Corp., was heated to 80° C. in a beaker on a hot plate until molten.

2. A Pressure Mixer Cell (FIG. 14C), supplied by Encapsulation Systems Inc., using a standard 4 blade mixer element was then heated to a jacket temperature of 90° C. throughout.

3. The mixer cell was enclosed by locking the lid to the mixer chamber in place. A mixer motor is installed at the top and this was kept bolted in place.

4. Pressure within the mixer chamber was raised to 40 psig by placing compressed air into the system.

5. The transducer of the ultrasonic homogenizer device, model number 600, supplied by Sonics & Materials Inc., was placed onto a stand within an enclosure comprised of tempered glass and a steel frame, over a magnetic stirrer/hot plate device.

6. The beaker containing the molten wax was placed atop the magnetic stirrer device.

7. A magnetic stir bar was then placed into the molten wax. The stirrer was caused to rotate steadily while the heating element of the hot plate was adjusted to maintain the temperature of the molten wax at 80° C.

8. Next, the transducer tip was lowered into the molten wax and held in place by a clamp. The transducer tip was kept immersed in the molten wax by maintaining the tip under the vortex created by the rotating stir bar.

9. 50 g of Choline Chloride solution, consisting of 70% active choline in 30% water, supplied by Ducoa Corp., wa then added to the molten wax under agitation.

10. The door to the enclosure was closed and the interior environment filled with nitrogen to 15 psig.

11. The ultrasonic homogenizer was set for 25 watts/cm**2 intensity at approximately 20 KHz frequency and was used to ultrasonically irradiate the molten wax/choline solution for 10 minutes.

12. The treated molten material was then delivered to the heated mixer cell pressurized to 40 psig, and agitated slowly. The temperature of the wax was monitored to maintain it in a molten state at least 10° C. above its melt point of 72° C. The molten wax was maintained at 82° C. for 30 minutes, while stirring.

13. After 30 minutes, heat was reduced and the wax permitted to cool to ambient temperature while stirring under 40 psig.

14. Pressure was released after one hour and the product inspected.

Inventor notes that choline chloride even in solution presents a strong fishy odor, but that this odor was not present in the final entrapped particle.

RESULTS

Product: a white free flowing powder with entrapped deposits of choline chloride. No fishy odor present. Applicant believes that water evaporated leaving deposits of the choline chloride remaining within the wax host matrix.

The total yield was 94.5% (236.25 g) from a 250 g starting run. With an initial liquid loading of 50 g, the total liquid loss was 13.75 g, or 27.5% of the starting composition by weight.

In the next experiment, only the pressurized mixer cell device of FIG. 14C was employed. The mixer 70 includes a mixer blade 71 powered by a motor 72 which was placed atop the mixer 70. The molten wax/liquid material 3 is placed in the interior agitation chamber of the mixer, entering the mixer through inlet channel 77. To pressurize the mixer 70, compressed air or other gases 38 enter through air inlet 73 and is trapped between inlet valve 74 and outlet valve 76 while liquid inlet valve 78 is also closed. A pressure gauge 75 measures the pressure within the mixer 70. The mixer may be heated by a heating jacket or heating coil (not shown). Agitation under pressure helps to disperse the liquid droplets within the wax host. The pressure helps to defeat evaporation of any volatiles within the liquid composition and the wax host itself.

Using the pressurized mixer only requires a few minutes to make an adequate dispersion of the liquid within the wax. By cooling the mixer housing 70 slowly, the wax is allowed to resolidify once the temperature within the mixer drops below the melt point of the wax. Continued agitation as the wax/liquid material cools helps to form solid particles which contain entrapped liquid droplets. After treatment, the product exits the mixer 70 through outlet 81 upon the opening of outflow valve 80.

The pressure cell mixer device of FIG. 14C can be substituted with the pressurized Sigma mixer (FIG. 14A) or the pressurized planetary mixer (FIG. 14B).

EXPERIMENT 9: PRESSURIZED MIXER SYSTEM USING CHOLINE LIQUID 1. 200 g of a vegetable trigliceride fat known as Dynasan 118, supplied by Huls America Corp., was heated to 80° C. in a beaker on a hot plate until molten.

2. A Pressure Mixer Cell (FIG. 14C), supplied by Encapsulation Systems inc., using a standard 4 blade mixer element was heated to a jacket temperature of 90° C.

4. The molten wax was then charged to the mixer cell device.

5. 50 g of Choline Chloride solution, consisting of 70% active choline in 30% water, supplied by Ducoa Corp., was then added to the molten wax within the mixer cell.

6. The mixer cell was then sealed and enclosed by locking the lid to the mixer chamber in place. A mixer motor was installed at the top and kept bolted in place. Agitation was started and maintained for the duration of the treatment.

7. Pressure within the mixer chamber was raised to 40 psig by injecting nitrogen into the mixer cell device.

8. The molten wax was treated in the pressurized mixer for 60 minutes while being agitated slowly. The temperature of the wax was monitored to maintain it in a molten state. The temperature of the molten wax was maintained at least 10° C. above its melt point 72° C.

9. After 60 minutes, heat was reduced and the wax permitted to cool to ambient temperature while stirring at 40 psig.

10. After one hour, pressure was released and the product inspected.

RESULTS

Product: a white free flowing powder with entrapped deposited choline chloride. No fishy odor was detected. Applicant believes that water evaporated leaving deposits of the choline chloride within the wax host matrix.

The total yield was 93% (232.54 g) from a 250 g starting run. The loss is attributed to the evaporation of the water component of the choline solution. With a starting liquid load of 50 g, the loss was 17.46 g or 34.9% by weight.

A comparison of the methods and results of Experiments 7 and 8 reveals that, while the use of a pressurized mixer apparatus alone is capable of entrapping liquids within waxes, the process is much more time consuming requiring at least 60 minutes of treatment and is incapable of transforming polymorphic waxes to an all beta state as confirmed through DSC spectra analyses. The resulting end-products are less stable than those treated by piston pressure and ultrasonic techniques. Additionally, it is clear that less liquid loss is experienced when these preferred embodiments of the subject invention are employed and especially when the pressurized mixer apparatus is combined with these processing techniques (see FIG. 8, for example).

To summarize the results of Experiments 1 through 8, above, maximum liquid loss due to volatilization during entrapment is experienced using an open bowl method and apparatus (Exp. 1). Liquid loss may be reduced by entrapping liquids under superatmospheric conditions (Exp. 8). Liquid losses may be further reduced by the subject piston pressurization or ultrasonic devices and methods of use (compare Exps. 7 and 8) and still further reduced when a pressurized mixer apparatus is used in combination with these devices (Exps. 2 and 3). Finally, it is clear that many liquids such as, for example, flavor oils (Exps. 2 and 3), Choline Chloride (Exps. 4, 7 and 8), catalysts (Exp. 5), and fire retardants (Exp. 6) may be successfully entrapped in various amounts within transformed waxes by the subject methods and apparatus.

While only a few examples have been provided in this specification, it should be obvious to anyone skilled in the art that other materials including fat/wax compounds of vegetable and animal derivatives, microcrystalline waxes and petroleum-based waxes may be enhanced through treatment in a pressure applicator device such as an ultrasonic system or a piston pressure applicator device described herein. It should also be appreciated that liquids other than those disclosed herein may be successfully entrapped within such lipoidal materials using the above method and apparatus.

While the method and apparatus of this invention have been discussed using as an example, glyceryl tristearate, it is clear that the invention is not limited to waxes which are normally solid at room temperature and which are useful for entrapment. The method and apparatus of this invention may be used with waxes which are liquid at ambient temperatures and which are then used in the transformed state for purposes other than encapsulation. Clearly, Applicant has discovered that the waxes, after being subjected to force, exist in a transformed liquid state having properties significantly different from those possessed before being subjected to the force. The transformed waxes of this invention may significantly change the manner and uses to which waxes are put in a wide variety of commercial processes. The transformed waxes may be put to such uses both in the solidified and liquid state after transformation. While Applicant has disclosed two preferred alternative apparatuses for subjecting the waxes to force, Applicant's discovery is clearly not limited to the two apparatuses described. The extent of Applicant's invention shall only be circumscribed by the following claims.

What is claimed is:

1. A method for entrapping liquids within a polymorphic wax and transforming the wax to a more stable crystalline state, comprising:
   a. melting the wax;
   b. adding a liquid to the melted wax;
   c. placing and confining the wax/liquid material in a chamber wherein it may be subjected to the action of a piston;
   d. subjecting said wax/liquid material in said chamber to at least one stroke of said piston; and
   e. permitting said wax to solidify.

2. A method for entrapping liquids within a polymorphic wax and transforming the wax to a more stable crystalline state, comprising:
   a. melting the wax;
   b. adding a liquid to the melted wax;
   c. subjecting said wax/liquid material to ultrasound; and
   d. permitting said wax to solidify.

3. The method of claim 1, wherein said wax is a polymorphic wax transformed by the method of claim 1 from its alpha to its beta form.

4. The method of claim 2, wherein said wax is a polymorphic wax transformed by the method of claim I from its alpha to its beta form.

5. The method of claim 1 carried out in an enclosed system under superatmospheric conditions such that volatilization of said liquid is minimized.

6. The method of claim 2 carried out in an enclosed system under superatmospheric conditions such that volatilization of said liquid is minimized.

7. A method for entrapping liquids within a polymorphic wax and transforming the wax to a more stable crystalline state, comprising subjecting the liquid and liquid wax to pressure and permitting the wax to solidify.

8. A method for entrapping liquids within a polymorphic wax and transforming the wax to a more stable crystalline state, comprising subjecting the liquid and liquid wax to a shock wave and permitting the wax to solidify.

9. A method for entrapping liquids within a polymorphic wax and transforming the wax to a more stable crystalline state, comprising subjecting the liquid and liquid wax to shear and permitting the wax to solidify.

10. A method for entrapping liquids within a polymorphic wax and transforming the wax to a more stable crystalline state, comprising subjecting the liquid and liquid wax to an abrupt pressure change and permitting the wax to solidify.

* * * * *

US005460756B1

REEXAMINATION CERTIFICATE (4071st)

United States Patent [19]
Redding, Jr.

[11] B1 5,460,756
[45] Certificate Issued   *May 2, 2000

[54] METHOD FOR ENTRAPMENT OF LIQUIDS IN TRANSFORMED WAXES

[75] Inventor: Bruce K. Redding, Jr., Philadelphia, Pa.

[73] Assignee: The Bryn Mawr Trust Company, Bryn Mawr, Pa.

Reexamination Request:
No. 90/005,466, Aug. 26, 1999

Reexamination Certificate for:
Patent No.: 5,460,756
Issued: Oct. 24, 1995
Appl. No.: 08/060,248
Filed: May 11, 1993

[ * ] Notice: This patent is subject to a terminal disclaimer.

Related U.S. Application Data

[63] Continuation-in-part of application No. 07/505,849, Apr. 6, 1990, Pat. No. 5,209,879.
[51] Int. Cl.$^7$ ............................ B29C 39/10; B29B 13/08; B29K 91/00
[52] U.S. Cl. .......................... 264/4; 204/157.62; 264/442; 425/174.2; 425/803
[58] Field of Search .................................. 264/4, 4.1, 442, 264/69, 325, 330, 345; 106/270, 271; 425/174.2, 803; 204/157.15, 157.42, 157.62

[56] References Cited

U.S. PATENT DOCUMENTS

| | | | |
|---|---|---|---|
| 5,601,865 | 2/1997 | Fulger et al. | 426/650 |
| 5,792,505 | 8/1998 | Fulger et al. | 426/650 |

OTHER PUBLICATIONS

Structural Investigations of β' Triacylglycerols: An X–Ray Diffraction and Microscopic Study of Twinned β' Crystals, Paul J.M.W.L. Birker, Sijmen de Jong, Eli C. Roljers and Ton C. van soest, JAOCS. vol. 68, No. 12., (Dec. 1991).
The Influence of Polymorphic Form on Oxygen and Water Vapor Transmission through Lipid Films, J.J. Kester and O. Fennema, JAOCS, vol. 66, No. 8 (Aug. 1989).

*Primary Examiner*—Mathieu Vargot

[57] ABSTRACT

The method and apparatus of this invention entraps liquids within wax and transforms naturally occurring or synthetic waxes into a state characterized by the fact that when the waxes solidify, they do so in forms different from those forms into which they would solidify except for the transformation. The entrapment and transformation is achieved by subjecting the waxes to force. As examples of apparatuses which can supply the force to effect the transformation, a piston apparatus and an ultrasonic apparatus are disclosed. The triglyceride waxes are one type of wax which may be transformed by the method and apparatus of this invention. Transformed triglyceride waxes are superior hosts for liquids entrapped within their matrix. The subject method is particularly effective for minimizing loss of liquids due to volatilization the entrapment process.

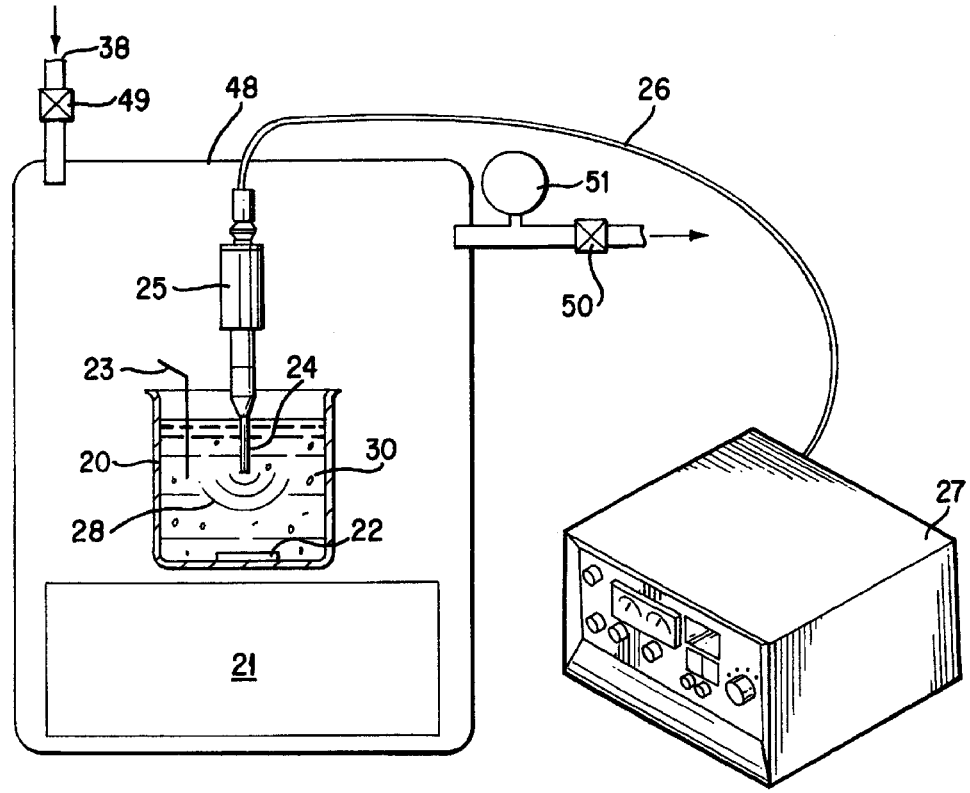

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–10 is confirmed.

New claim 11 is added and determined to be patentable.

*11. The method of claim 7 wherein the liquid wax is subjected to a first pressure which transforms the liquid wax to a form capable of assuming a more stable crystalline state when solidified and thereafter subjecting the liquid wax and the liquid to a second pressure while mixing and permitting the liquid wax to solidify, wherein said second pressure is superatmospheric such that volatilization of said liquid is minimized.*

\* \* \* \* \*